(12) United States Patent
Morgan et al.

(10) Patent No.: US 9,149,544 B2
(45) Date of Patent: Oct. 6, 2015

(54) BIOCONJUGATION OF CALCIUM PHOSPHOSILICATE NANOPARTICLES FOR SELECTIVE TARGETING OF CELLS IN VIVO

(75) Inventors: Thomas T. Morgan, Pepperell, MA (US); Brian M. Barth, Elizabethtown, PA (US); James H. Adair, State College, PA (US); Rahul Sharma, Baton Rouge, LA (US); Mark Kester, Harrisburg, PA (US); Sriram S. Shanmugavelandy, Hershey, PA (US); Jill P. Smith, Camp Hill, PA (US); Erhan I. Altinoglu, Boston, MA (US); Gail L. Matters, Hummelstown, PA (US); James M. Kaiser, Harrisburg, PA (US); Christopher McGovern, Harrisburg, PA (US)

(73) Assignee: THE PENN STATE RESEARCH FOUNDATION, State College, PA (US)

( * ) Notice: Subject to any disclaimer, the term of this patent is extended or adjusted under 35 U.S.C. 154(b) by 427 days.

(21) Appl. No.: 12/941,719

(22) Filed: Nov. 8, 2010

(65) Prior Publication Data
US 2011/0129413 A1    Jun. 2, 2011

Related U.S. Application Data

(60) Provisional application No. 61/258,664, filed on Nov. 6, 2009.

(51) Int. Cl.
| A61K 49/00 | (2006.01) |
| A61K 41/00 | (2006.01) |
| A61K 47/48 | (2006.01) |

(52) U.S. Cl.
CPC ......... *A61K 49/0093* (2013.01); *A61K 41/0057* (2013.01); *A61K 47/48861* (2013.01); *A61K 49/0034* (2013.01); *A61K 49/0043* (2013.01)

(58) Field of Classification Search
None
See application file for complete search history.

(56) References Cited

U.S. PATENT DOCUMENTS

| 6,599,928 B2 | 7/2003 | Kunz et al. |
| 2005/0025820 A1 | 2/2005 | Kester et al. |
| 2005/0281884 A1 | 12/2005 | Adair et al. |
| 2006/0153860 A1 | 7/2006 | Cho et al. |
| 2007/0292495 A1 | 12/2007 | Ludwig et al. |
| 2008/0220042 A1 | 9/2008 | Hashi et al. |

FOREIGN PATENT DOCUMENTS

WO    WO 2007144644 A2 * 12/2007

OTHER PUBLICATIONS

Nobs et al. Current methods for attaching targeting ligands to liposomes and nanoparticles. 2004 J. Pharm. Sci. 93: 1980-1992.*
Behr et al. Targeting of cholecystokinin-B/gastrin receptors in vivo: preclinical and initial clinical evaluation of the diagnostic and therapeutic potential of radiolabelled gastrin. 1998 Eur. J. Nucl. Med. 25: 424-430.*
Morgan et al. Encapsulation of Organic Molelclules in Calcium Phosphate Nanocomposite Particles for Intracellular Imaging and Drug Delivery.Nano Letters 2008, 8,(12),4108-4115.
Altinoglu et al. Near-Infrared Emitting Fluorophore-Doped Calcium Phosphate Nanoparticles for in Vivo Imaging of Human Breast Cancer. ACS Nano 2008,2,(10) 2075-2084.
Kester et al. Calcium Phosphate Nanocomposite Particles for in Vitro Imaging and Encapsulated Chemotherapeutic Drug Deliver to Cancer Cells. Nano Letters 2008, 12,4116-4121.
Smith et al. Characterization of the CCK-B/Gastrin-Like Receptor in Human Colon Cancer. Am J Physiol 1996, 271, R796-R805.
Smith et al. Identification and Characterization of CCK-B/Gastrin Receptors in Human Pancreatic Cancer Cell Lines. Am.J. Physiol. 1994, 266, R277-R283.

* cited by examiner

*Primary Examiner* — Nissa Westerberg
*Assistant Examiner* — Jennifer Lamberski
(74) *Attorney, Agent, or Firm* — Laurence Weinberger

(57) ABSTRACT

Non-aggregating resorbable calcium phosphosilicate nanoparticles (CPNPs) are bioconjugated to targeting molecules that are specific for particular cells. The CPNPs are stable particles at normal physiological pH. Chemotherapy and imaging agents may be integrally formed with the CPNPs so that they are compartmentalized within the CPNPs. In this manner, the agents are protected from interaction with the environment at normal physiological pH. However, once the CPNPs have been taken up, at intracellular pH, the CPNPs dissolve releasing the agent. Thus, chemotherapeutic or imaging agents are delivered to specific cells and permit the treatment and/or imaging of those cells. Use of the bioconjugated CPNPs both limits the amount of systemic exposure to the agent and delivers a higher concentration of the agent to the cell. The methods and principals of bioconjugating CPNPs are taught by examples of bioconjugation of targeting molecules for breast cancer, pancreatic cancer, and leukemia.

2 Claims, 14 Drawing Sheets

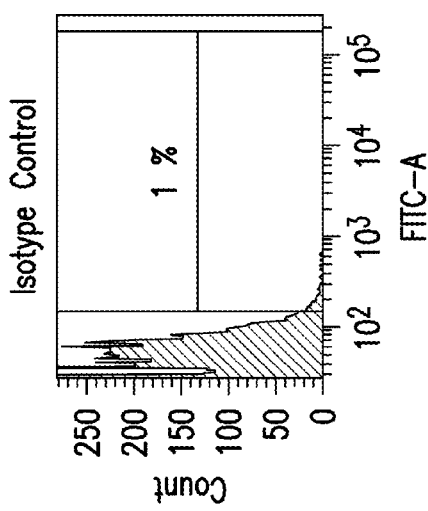
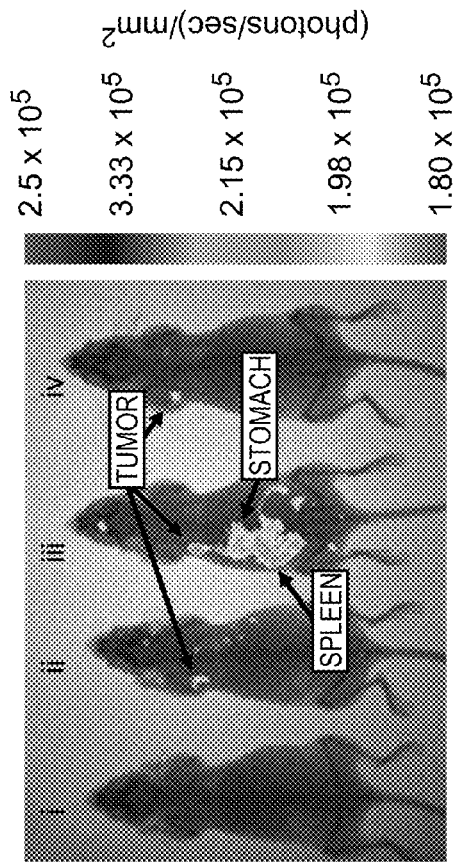
FIG. 5A
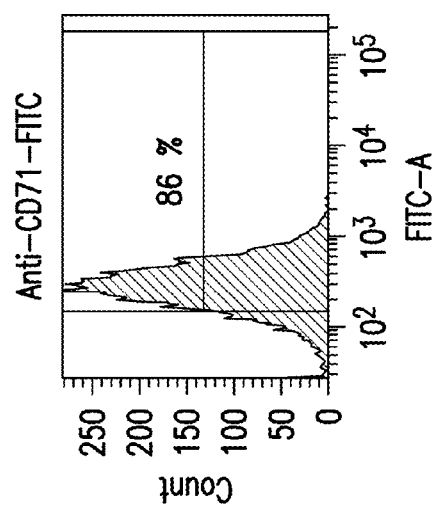
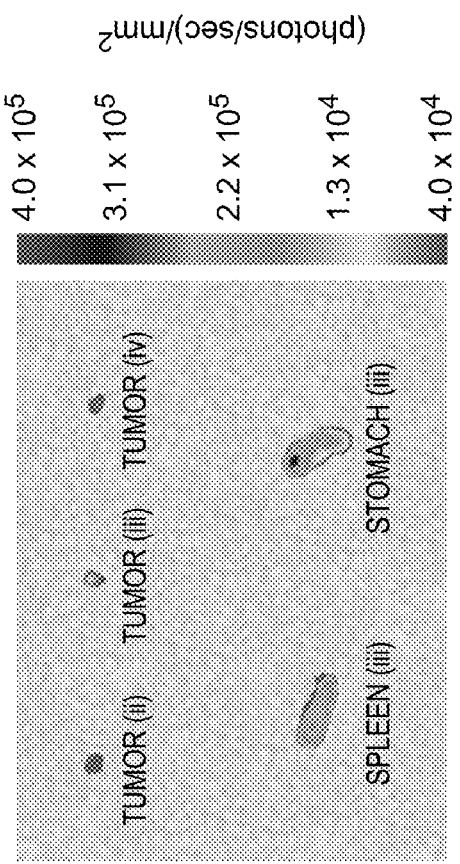
FIG. 5B
FIG. 5C

BIOCONJUGATION OF CALCIUM PHOSPHOSILICATE NANOPARTICLES FOR SELECTIVE TARGETING OF CELLS IN VIVO

Benefit of U.S. Provisional Application No. 61/258,664 filed on Nov. 6, 2009 is hereby claimed.

This invention was made with government support under Grant No. CA117926, awarded by the National Institutes of Health. The Government has certain rights in the invention.

BACKGROUND

1. Field of the Invention

The present invention relates to the formation and use of bioresorbable calcium phosphosilicate nanoparticles bioconjugated to molecules that selectively target cells in vitro and in vivo.

2. Description of the Art

The early diagnosis of cancer is the critical element in successful treatment and long term favorable patient prognosis. The high mortality rate, in particular, for pancreatic cancer is primarily attributed to the tendency for late diagnoses as symptoms typically occur after the disease has metastasized as well as the lack of effective systemic therapies. For breast cancer, late diagnosis is often associated with the lack of timely sensitive imaging modalities. The promise of nanotechnology is presently limited by inability to simultaneously seek, treat, and image cancerous lesions.

Despite many new advances in the arsenal of antineoplastic agents, drug resistant, highly metastatic cancers continue to ravage patients[21]. As examples, breast cancer is still the second leading cause of death in American women with an estimated 192,370 cases diagnosed in 2009. In this year alone, about 40,610 women will die from breast cancer in the United States. Pancreatic cancer is the fourth leading cause of cancer related deaths in the United States. Approximately 42,470 Americans were diagnosed with pancreatic cancer in the past year, and nearly 100% will succumb to this disease[21]. It is clear that new modalities must be developed that have the capabilities to both improve diagnosis and treatment of cancers. The term "theranostic" has been coined to describe modalities that can simultaneously diagnose and treat.

As described in U.S. patent application Ser. Nos. 10/835,520 and 11/142,913, calcium phosphosilicate nanoparticles (CPNPs) have been engineered to be a resorbable non-toxic vehicle for the delivery of a diversity of therapeutic and imaging agents in biological systems[1-4]. Previous studies have shown that encapsulation within CPNPs improved the lifetime and quantum properties of fluorescent dyes[1, 4]. Initial in vivo imaging trials demonstrated that CPNPs, functionalized with polyethylene glycol (PEG) moieties, accumulated within solid tumors via an enhanced permeation retention (EPR) effect[2]. While EPR serves as an effective passive targeting strategy, particular interest lies in the ability to actively target cancerous cells to deliver antineoplastic agents, thereby decreasing effective dosage and limiting off-target toxicity.

CPNPs are nontoxic, colloidally stable, resorbable, non-aggregated nanoscale vehicles that deliver chemotherapeutics, gene therapy, and imaging agents. Two exciting aspects of CPNPs as drug delivery vehicles include enterohepatic biliary excretion that minimizes hepatic toxicity and pH-triggered release of active agents. At pH 7.4, the CPNPs are sparingly soluble, but the CPNPs dissolve in the late stage endolysosomes at pH 4 to 5[1,4]. The pH response of CPNPs has two distinct advantages. First, it permits a decrease in the effective dose of chemotherapeutic drugs, which are often toxic, required for optimal therapeutic benefit by increasing the efficiency of drug delivery into cancer cells[3]. Second, sequestering the drug in the CPNPs decreases the effective concentration of free drug present in the extracellular fluid where the pH is maintained at approximately 7.4 by physiological buffers. This compartmentalization feature for drug delivery is a distinct advantage since acute systemic toxicity to normal cells is limited. Moreover, off site cytotoxicity may be further ameliorated with target and tissue-specific CPNPs.

Scientific investigations have identified cancer cell specific markers with unique phenotypes that can be exploited to target tumors as will be described in this patent document. Of particular interest is the prevalence of transferrin receptors (CD71) on cancerous cells, including breast cancer[5-9]. The transferrin receptor is responsible for transporting iron, via interaction with transferrin, into cells as demanded by metabolic need[5, 6]. Accordingly, transferrin receptors are found predominately on proliferating cells with elevated metabolic levels, including many cancerous cells, as well as brain capillary endothelial cells, and hematopoietic cells[10, 11]. In a manner similar to CD71, gastrin receptors have a predominate prevalence within certain tissues, specifically the gastrointestinal and central nervous systems[12-14]. The hormone gastrin binds to a family of G-protein-coupled receptors, also known as the cholecystokinin-2 ($CCK_2$ or CCK-B) receptor family[14, 15], and is typically known as a key mediator of stomach acidity[16] and growth of the gastrointestinal tract[17]. Intriguingly, $CCK_2$ receptor expression is often increased in many cases of gastrointestinal cancer[14, 18] including pancreatic cancer[19] and, in particular, an increase in expression of a specific splice variant ($CCK_{2i4sv}$ or CCK-C) of the receptor[20].

The inventive bioconjugated particles and bioconjugation approaches taught in this patent document may also be used with non-solid tumors. Leukemia is one of the most common and aggressive adult cancers as well as the most prevalent childhood cancer. Leukemia stem cells (LSCs) have been hypothesized to be responsible for cancer development, relapse, and resistance to treatment, and new therapeutics targeting these cellular populations are urgently needed. Recently, studies have indicated that LSCs reside within a lineage$^-$Sca-1$^+$CD117 cellular population in human patients and animal models of chronic myeloid leukemia (CML) and therefore present a target for intervention.

Accordingly, as outlined above, there is a significant medical need in the field of disease treatment for nanoparticle compositions capable of targeted systemic delivery of imaging and/or therapeutic agents as well as imaging and treatment methods employing such nanoparticles.

BRIEF DESCRIPTION OF THE DRAWINGS

For the purpose of illustrating the invention, there are shown in the drawings exemplary embodiments of the invention; however, the invention is not limited to the specific methods, compositions, and devices disclosed. In addition, the drawings are not necessarily drawn to scale.

FIG. 5A-C illustrates targeting transferrin receptors in an in vivo subcutaneous-tumor model of breast cancer. Human MDA-MB-231 metastatic breast cancer cells were xenografted subcutaneously into athymic nude mice. One week following engraftment, ICG-loaded CPNPs were administered systemically via tail vein injection and near-infrared images were taken 24 hours post-injection. 5A: flow cytometry demonstrating the presence of the transferrin CD71 receptor. 5B: Near-infrared images taken 96 h post injection. From left to right, mice received: (i) free ICG, (ii) ICG-loaded, PEG-CPNPs, (iii) ICG-loaded, anti-CD71-Avidin-CPNPs, and (iv) ICG-loaded, Human Holotransferrin-Avidin-CPNPs. 5C: Excised tumors (mice ii, iii, and iv), excised spleen (mouse iii), and excised stomach (mouse iii). All images are representative of four independent experiments.

DETAILED DESCRIPTION OF THE INVENTION

It is to be understood that this invention is not limited to the specific devices, methods, applications, conditions or parameters described and/or shown herein, and that the terminology used herein is for the purpose of describing particular embodiments by way of example only and is not intended to be limiting of the claimed invention. It is to be appreciated that certain features of the invention, which are, for clarity, described herein in the context of separate embodiments, may also be provided in combination in a single embodiment. Conversely, various features of the invention that are, for brevity, described in the context of a single embodiment, may also be provided separately or in any subcombination.

This patent document describes the design and synthesis of resorbable bioconjugated calcium phosphosilicate nanocomposite particles (CPNPs) that can be systemically targeted to biological tissues by the attachment of appropriate molecular moieties that specifically recognize and bind to the target tissues. The general methodology for synthesizing and using these bioconjugated CPNPs is disclosed through three example bioconjugation techniques. Using these techniques, fluorescently labeled CPNPs are described that 1): systemically target breast cells; 2) systemically target pancreatic cancer lesions; and 3) systemically target leukemia stem cells. A fluorescent label incorporated into the CPNPs permits identification of the location of binding of the CPNPs in breast and pancreatic cancers, and, in the case of leukemia stem cells, the photodynamic destruction of the cells. As taught in the prior art[3] other agents including chemotherapeutic agents can be incorporated into the CPNPs in place of or alongside ICG. Thus, the bioconjugated CPNPs taught in this patent document can be utilized both for identification of the presence and location of diseased tissue as well as the treatment of diseased tissue by the targeted delivery of therapeutic agents.

The bioconjugated CPNPs used for purpose of disclosure in this patent document comprise a ~20 nm diameter composite particle composed of an amorphous calcium phosphate matrix doped with silicate in which a near infra-red imaging agent, indocyanine green (ICG) is embedded. The following three coupling strategies for bioconjugation to CPNPs are described and their use is disclosed herein in the following exemplary embodiments:

- CPNP-Avidin non-covalently bonded to biotinylated anti-CD71
- CPNP-Avidin non-covalently bonded to biotinylated human holotransferrin ligand
- CPNP-Avidin non-covalently bonded to biotinylated pentagastrin
- CPNP-PEG (maleimide-coupled) covalently bonded to gastrin-10
- CPNP-PEG (sulfo-NHS-coupled) covalently bonded to anti-CD117
- CPNP-PEG (sulfo-NHS-coupled) covalently bonded to anti-CD96

Example 1

Avidin Biotin Coupling

Figure 1A:
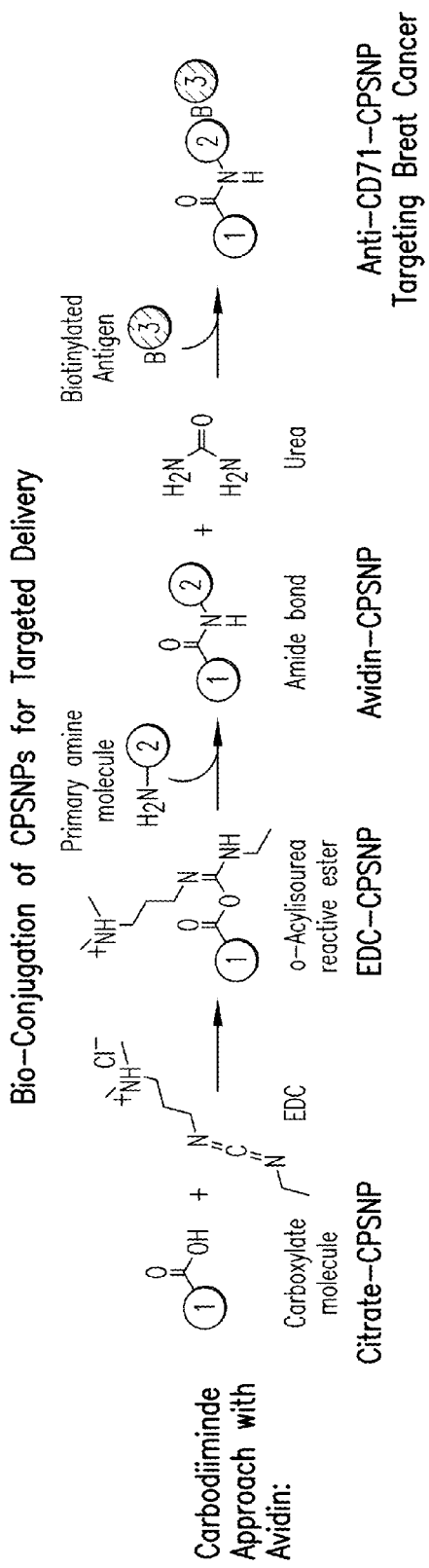
FIGS. 1A, 1B, and 1C schematically outline non-covalent (1A) and covalent (1B and 1C) methods for bioconjugating targeting molecular moieties to CPNPs.

The first coupling strategy schematically outlined in FIG. 1A employs an avidin molecule coupled to citrate functionalized CPNPs. (A variety of carboxylate surface functionalizations may be used in the preparation of the CPNPs. Citrates are considered particularly suitable sources of carboxylate surface functionalization. In some embodiments, the surface functionalization (e.g., citrate) is specifically adsorbed to the calcium phosphosilicate nanoparticle. Avidin has four potential binding sites for biotin. As is well known in the art, many biotinylated biological molecules of interest are available that can be used to target specific cell types. An avidin-CPNP is described that can be used to non-covalently bioconjugate targeting biological molecules to the CPNPs by coupling the biotinylated targeting molecule of interest to avidin-CPNPs. In this patent document three working examples describe CPNP bioconjugation to human holotransferrin, anti-CD71 antibody, and a short gastrin polypeptide (pentagastrin) by means of avidin-biotin coupling strategies. The conjugation of biotinylated human holotransferrin (diferric transferrin), biotinylated anti-CD71 antibody (antitransferrin receptor antibody), and biotinylated pentagastrin to avidin conjugated CPNPs (avidin-CPNPs) permitted the attempted targeting of transferrin receptors, which are highly expressed on breast cancer cells. In a similar manner, the conjugation of biotinylated pentagastrin to avidin-CPNPs permitted the attempted targeting of $CCK_2$ receptors.

Example 2

Maleimide Covalent Coupling

Figure 1B:
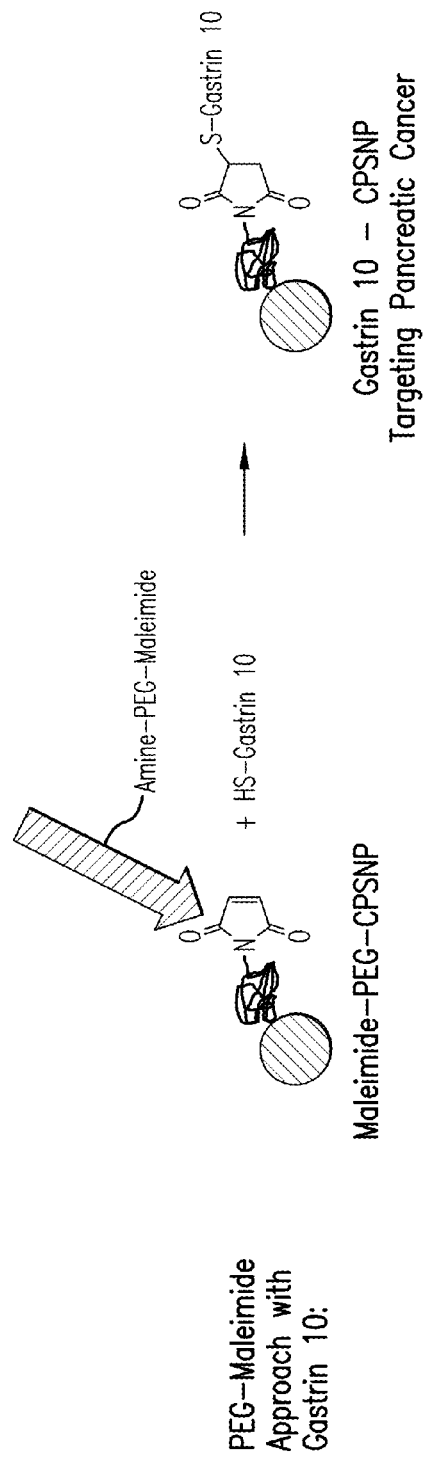

A second covalent coupling strategy schematically outlined in FIG. 1B uses a PEG-maleimide reaction to bioconjugate a targeting molecule and is exemplified by the coupling of decagastrin (gastrin-10). Targeting molecular moieties suitable for use with this method include those having a sulfhydryl-group such as antibodies, peptides, ligands, receptors, and the like. Citrate functionalized CPNPs are reacted with a carbodiimide and a maleimide polyethylene glycol amine to yield a CPNP comprising a surface moiety having a maleimide terminal group that can then be reacted with a binding moiety having a sulfhydryl group. Ethyl-N-(3-dimethylaminopropyl)-N' hydrochloride carbodiimide is considered especially suitable for the disclosed method for the carbodiimide linker group. The maleimide group is suitably bound to the surface of the nanoparticle, but can, in some embodiments, be bound to the binding moiety. PEG-maleimide coupling of decagastrin (gastrin-10) to PEG-CPNPs also permits targeting of gastrin receptors, which are over-expressed in pancreatic cancer lesions, but not normal pancreas. Maleimide coupling of gastrin to a targeting peptide is described in the prior art[35], but the present invention of using maleimide chemistry to couple a targeting moiety to a resorbable non-aggregating CPNP incorporating an imaging or therapeutic agent is not taught or anticipated by the prior art.

Example 3

Covalent Coupling via N-Hydroxysulfosuccinimide (Sulfo NHS)

Figure 1C:
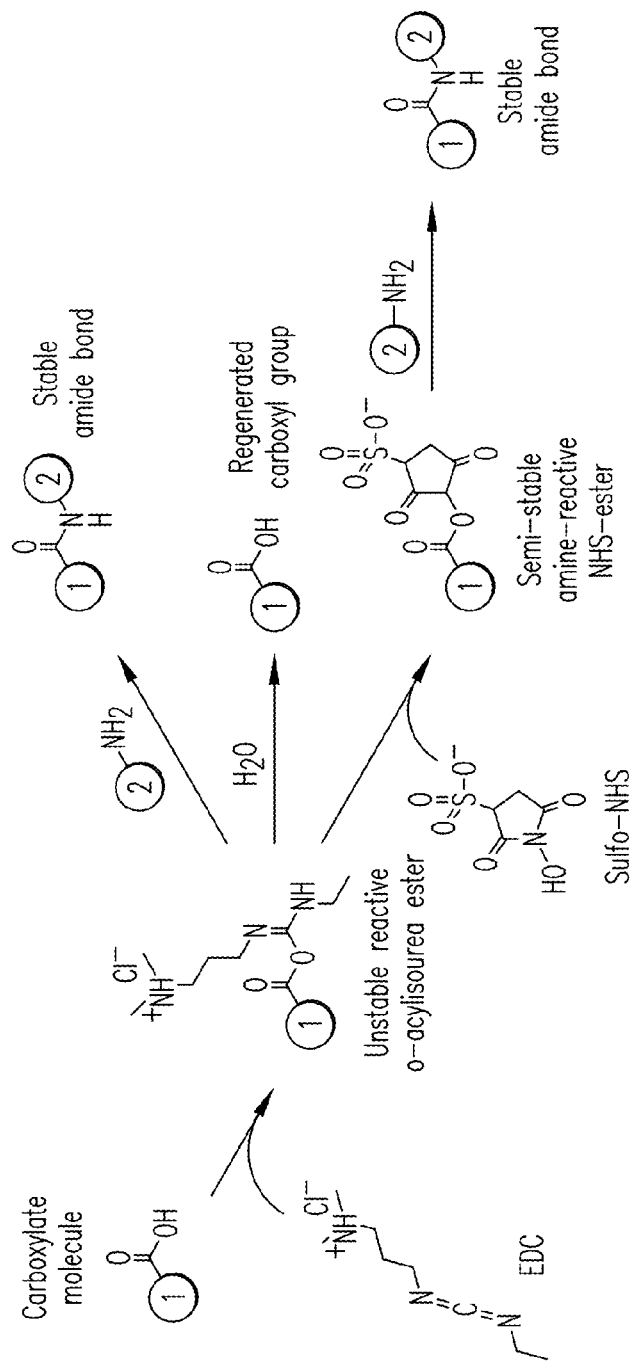

The bioconjugation of anti-CD96 and anti-CD117 antibodies and other targeting moieties not possessing a thiol group requires a different approach since the maleimide-coupling approach relies on the availability of thiol groups on the molecule to be conjugated, which if unavailable, necessitates thiol introduction under conditions that may jeopardize the integrity of the biomolecules. To avoid this potential problem and provide a generalized coupling method that does not rely on the availability of thiol groups, a third coupling strategy outlined in FIG. 1C was developed that utilizes a multistep synthesis using EDAC and Sulfo NHS.

As will be appreciated by those skilled in the art, targeting molecular moieties suitable for bioconjugation may include antibodies, polypeptides, nucleic acids such as siRNAs, ligands, receptors and those moieties that target signaling proteins, angiogenesis factors, metalloproteases, and the like. Generally, the targeting moieties may be chosen on the basis of their ability to bind specifically to a particular tissue such as a cancerous cell and/or cancerous lesion.

All these bioconjugated CPNPs have the potential to perform as a theranostic modality, simultaneously enhancing drug delivery, targeting, and imaging of breast, pancreatic, and leukemic cancers.

Figure 2:
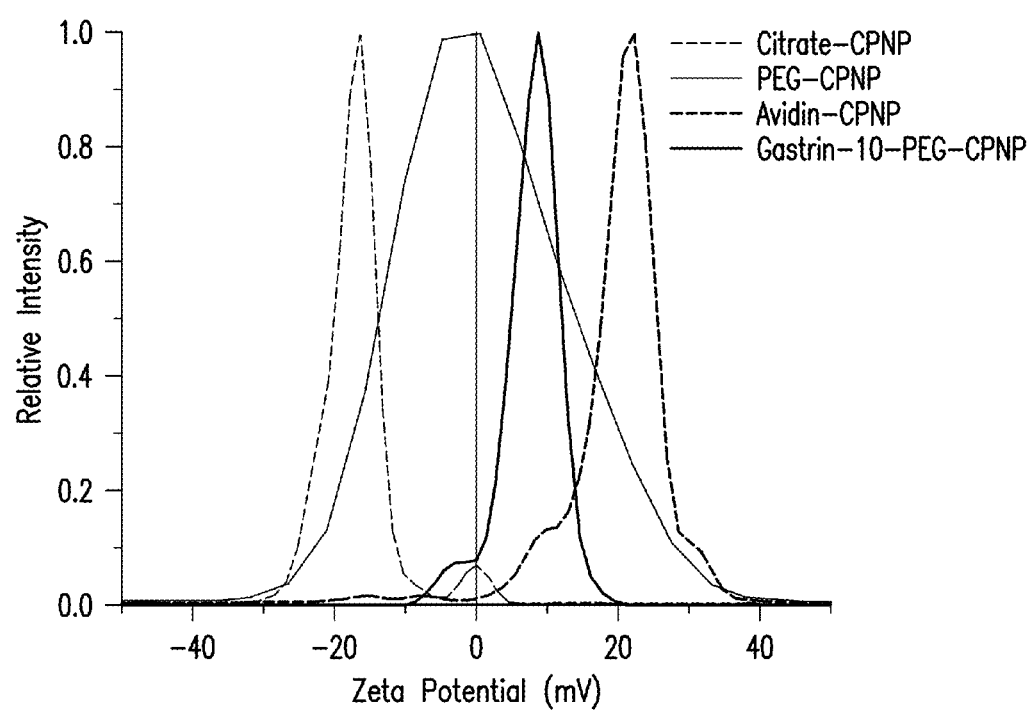
FIG. 2 illustrates Zeta potential distributions for citrate-CPNPs, Avidin-CPNPs, PEG-CPNPs, and gastrin-10-PEG-CPNPs. The citrate-CPNPs displayed a mean zeta potential of −16±1.3 mV, whereas PEGylation shifted the mean zeta potential to +3.0±2.0 mv, gastrin-10 conjugation further shifted the mean zeta potential to +6±3.2 mv, and the avidin- CPNPs had a mean zeta potential value of +29±8.7 mV. All zeta potential distributions are representative of three independent experiments.

Physical Characterization of CPNPs:

Citrate functionalized CPNPs were utilized as a platform for avidination (see experimental procedures below for description of bioconjugation schemes such as avidination) which allowed the characterization of bioconjugation via zeta potential analysis. FIG. 2 shows the zeta potential distribution of: 1) citrate-CPNPs prior to bioconjugation with avidin; 2) of the avidin-CPNPs complex; 3) maleimide-terminated polyethylene glycol (PEG)-coated CPNPs; and 4) CPNPs conjugated with gastrin-10 via a maleimide-PEG coupling. Prior to bioconjugation with avidin, the Citrate-CPNPs display a negative mean zeta potential value of −16±1.3 mv, which is consistent with previous reports[1]. However, after bioconjugation with avidin, the Avidin-CPNPs displayed a relatively high positive mean zeta potential value of +29±8.7 mv. The isoelectric point for avidin is pH 10. Thus, the shift from a negative zeta potential to a positive zeta potential distribution is strong evidence of avidin bioconjugation on the surface of CPNPs. Also, FIG. 2 shows the shift in mean zeta potential to +3.0±2.0 mv when coated with the PEG and then a further shift to +6±3.2 mv when conjugated to gastrin-10.

Figure 3:
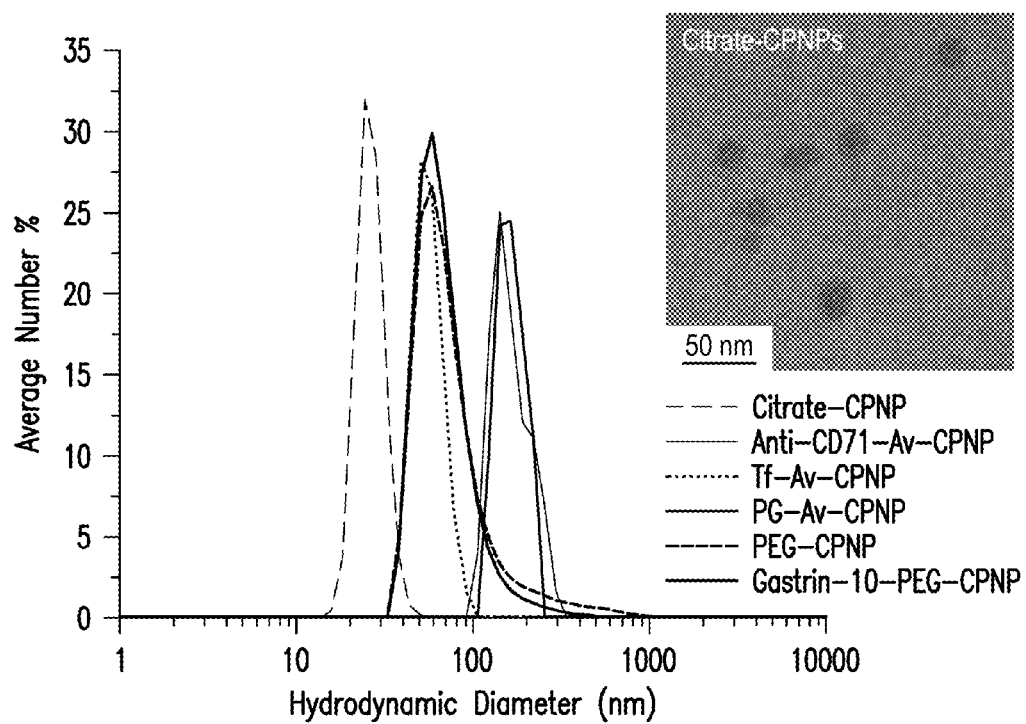
FIG. 3 shows dynamic light scattering determinations for citrate-CPNPs, anti-CD71-Avidin-CPNPs (Anti-CD71-AV-CPNP), Human Holotransferrin-Avidin-CPNPs (Tf-Av-CPNP), Pentagastrin-Avidin-CPNPs (PG-Av-CPNP), maleimidePEG-CPNPs (Peg-CPNP), and gastrin-10-maleimidePEG-CPNPs (gastrin-10-PEG-CPNP). All dynamic light scattering determinations are the mean of three independent experiments. Inset shows a typical TEM micrograph of Citrate-CPNPs.

Further characterization confirmed the presence and bioactivity of the bioconjugated Avidin-CPNPs for biotin. A 2,6-ANS titration was used to confirm both the presence of avidin and it associated bioactivity. An analysis of the particle size distributions of the nanoparticles by means of dynamic light scattering (DLS) as shown in FIG. 3 revealed that all the various bioconjugated CPNPs had a larger mean hydrodynamic diameter that the non-bioconjugated citrate-CPNPs. Additional characterization was performed using transmission electron microscopy (TEM). Transmission electron microscopy analysis indicated that the inorganic particle size was in the range from 10 to 30 nm for all of the CPNPs (see inset in FIG. 3). The smaller size indicated by TEM relative to DLS analyses is consistent with the ability to determine the solid material diameter by the TEM technique in contrast to DLS which gives the hydrodynamic size distribution in colloidal suspension of solid particle, organic layers, and surrounding liquid.

Figure 4A:
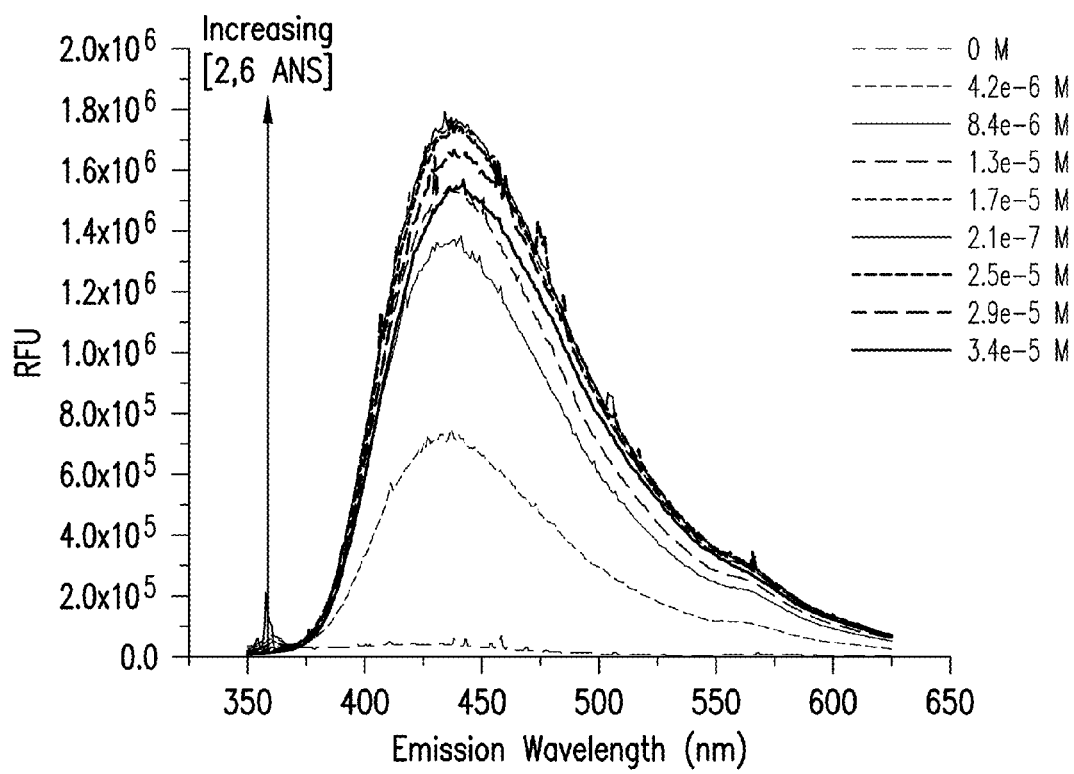
FIG. 4 A-D illustrates the binding and displacement of 2,6-ANS utilized to evaluate the coupling of biotin to avidin-CPNPs. 4A: Fluorescence intensities for the first step of the 2,6-ANS assay. The addition of 2,6-ANS to the avidin-CPNP complex results in a six fold increase in fluorescence as the fluorescent probe binds to the biotin binding site on avidin. The 2,6-ANS was added at increasing concentrations to avidin-CPNPs and increased fluorescence, indicative of 2,6-ANS bound to avidin, was quantitatively determined. 4B: Peak height of fluorescence shown on FIG. 4A as a function of 2,6-ANS molarity. 4C: Fluorescence intensities for the second step of the 2,6-ANS assay. The addition of biotin to the 2,6-ANS-Avidin-CPNP complex results in a decrease in fluorescence as biotin displaces the fluorescent probe from the biotin binding site on avidin. Biotin was added at increasing concentrations to the 2,6-ANS-Avidin-CPNP complex and a decrease in fluorescence, indicative of biotin displacing 2,6-ANS, was quantitatively determined. 4D: Peak height of fluorescence shown on FIG. 4C as a function of biotin molarity. All determinations are representative of three independent experiments.
Figure 4B:
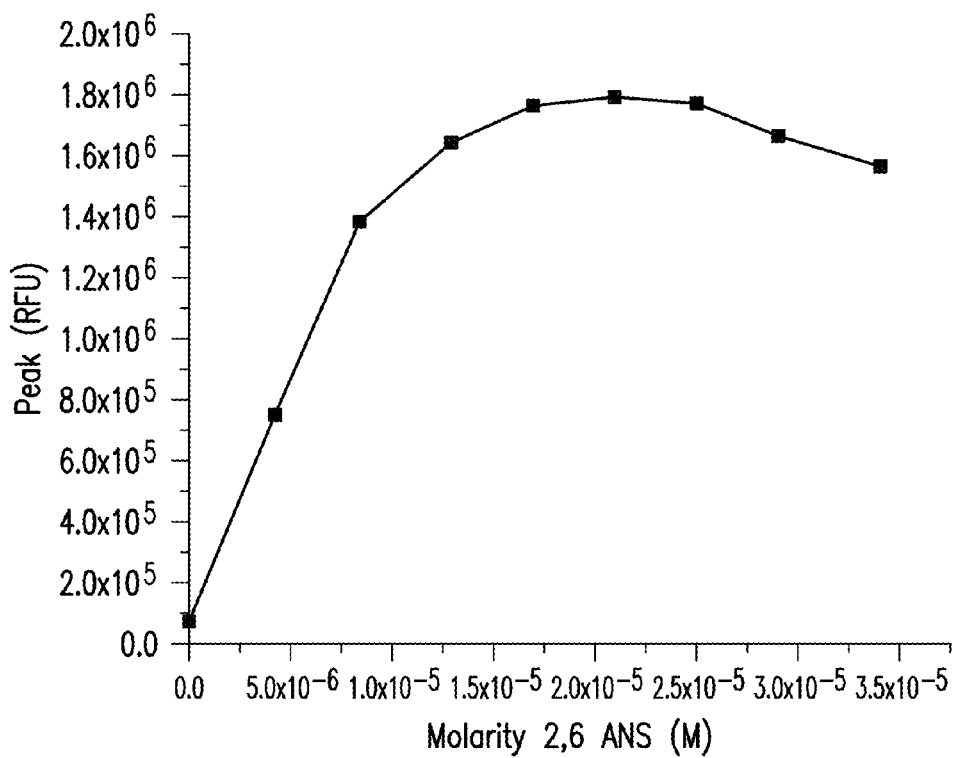
Figure 4C:
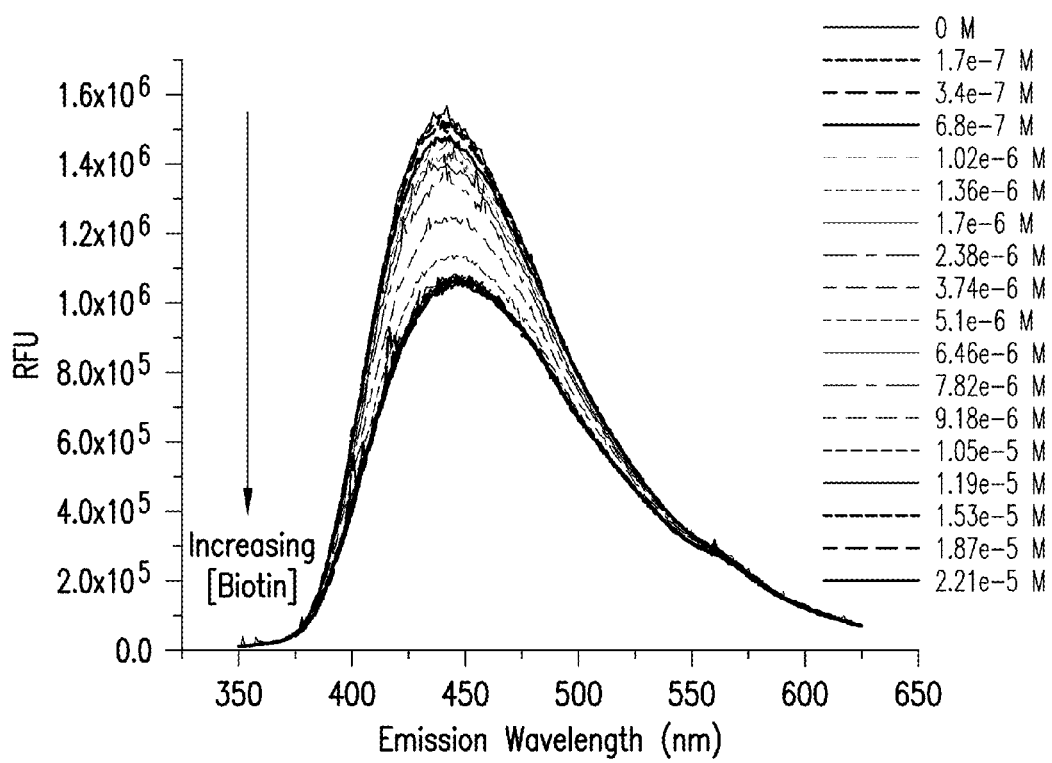
Figure 4D:
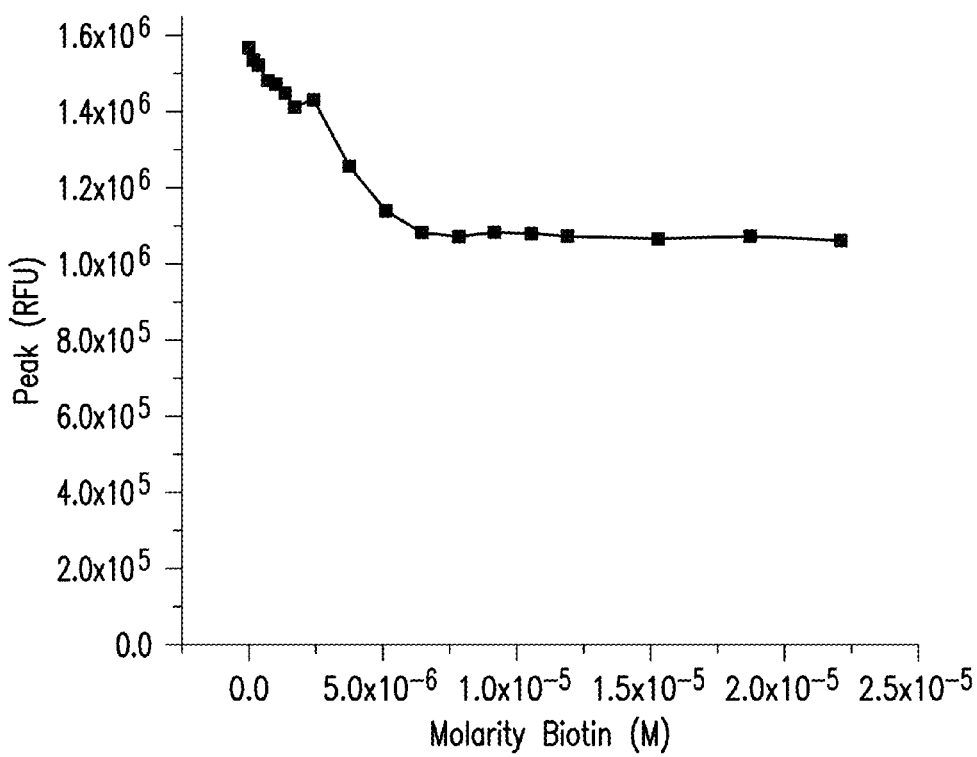

Previous studies have demonstrated that a 2,6-ANS assay can be utilized to evaluate the biotin-binding functionality of avidin[22]. The 2,6-ANS fluorescent probe binds to avidin, an event that can be measured using fluorescence spectroscopy. Without avidin present, the 2,6-ANS fluorescent probe displays low fluorescence intensity. In the presence of avidin, the binding of 2,6-ANS to the biotin-binding site on avidin produces an increase in fluorescence intensity. 2,6-ANS added in increasing concentrations to the avidin-CPNPs yielded a concentration-dependent increase in 2,6-ANS fluorescence emission (see FIGS. 4A and 4B). The titration of 2,6-ANS showed an increase in fluorescence up to $1.79 \times 10^6$ RFU after the addition of 34 µM 2,6-ANS. Beyond this point of maximum fluorescence intensity, 2,6-ANS self-quenched, at which point biotin was added to displace the 2,6-ANS. Biotin has a greater affinity for the biotin-binding site on avidin than does the 2,6-ANS fluorescent probe. Therefore, biotin additions to the 2,6-ANS-Avidin-CPNP complex displaces the 2,6-ANS from the biotin-binding site on avidin. Since the 2,6-ANS fluorescent probe displays minimal fluorescence when it is not bound to avidin, this displacement produces a decrease in fluorescence (FIGS. 4C and 4D) to a plateau of $1.08 \times 10^6$ RFU after the addition of 1.90 nM biotin. The plateau is present in FIG. 4D because of the intrinsic fluorescence of 2,6-ANS. This result demonstrates the successful coupling of biotin to the Avidin-CPNPs. The 2,6-ANS fluorescence emission did not decrease completely as some 2,6-ANS remains bound to the Avidin-CPNPs. While the affinity of avidin for biotin is high, residual reactants and ionic conditions can influence this affinity as it has been established that water participates in displacing biotin from the binding pocket of avidin, or similar proteins[23, 24]. Nonetheless, this analysis successfully demonstrates that the Avidin-CPNPs are biofunctional, through binding of 2,6-ANS as well as its displacement by biotin. One or more of the four avidin binding sites for biotin may be occupied when a biotinylated targeting molecule is bound to avidin, the exact number depending on the location of the avidin on the CPNP and the orientation and size of the biotinylated molecule.

Figure 6:
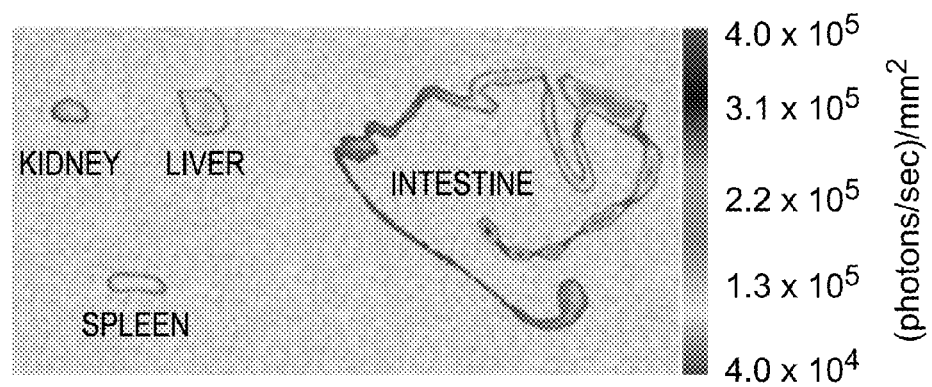
FIG. 6 illustrates ICG-loaded PEG-CPNP clearance via hepatobiliary secretion. Twenty-four hours post-tail vein injection, the kidney, liver, spleen, and intestine were excised and imaged. Increased signal is seen toward the end of the intestine as indicated by fecal pellets within the intestine. All images are representative of three independent experiments.

Evaluation of Breast Cancer-Targeted CPNPs In Vivo:

Transferrin receptors are expressed on cells with increased metabolic demand, including several cancerous cells. The presence of the transferrin receptor (CD71) on the surface of human MDA-MB-231 cells was determined via flow cytometry and was found to be prevalent on nearly all cells analyzed (FIG. 5A). The presence of CD71 on most MDA-MB-231 cells indicated that it would be an ideal surface target, exploited by coupling specific antibodies, or the ligand holotransferrin, to demonstrate the utility of bioconjugated Avidin-CPNPs. It has been previously shown that the untargeted PEG-CPNPs passively accumulate in breast cancer tumors via the EPR effect[2]. This finding was successfully repeated by the present inventors as a positive control (FIG. 5B). Intriguingly, only tumors from mice receiving anti-CD71-Avidin-CPNPs, and not Human Holotransferrin-Avidin-CPNPs or untargeted PEG-CPNPs, were effectively targeted as evidenced by prominent infrared stimulated florescence of ICG at 96 h following tail vein injection of CPNPs (FIG. 5B). It has been reported, and is likely in this circumstance, that the transferrin receptors are saturated with transferrin[25] and therefore are unable to bind the Human Holotransferrin-Avidin-CPNPs. This is also supported by the success of the anti-CD71-Avidin-CPNPs, which recognize an epitope separate from the ligand-binding site on the transferrin receptor. Importantly, the anti-CD71-Avidin-CPNPs were more effective at targeting the tumors than the passively accumulating PEG-CPNPs based on the relative fluorescence intensity. However, and not surprisingly, the effective targeting was not limited to the tumors, but also to the spleen, which is rich in a diversity of hematopoietic cells (FIG. 5C). It was also observed that there was some off-target staining of the stomach (FIG. 5C), possibly due to avidin interaction with biotin ingested as part of the mouse's diet or due to the presence of transferrin receptors on these tissues. Previously, clearance of PEG-CPNPs was reported to occur via hepatobiliary clearance evidenced by predominant staining of the liver within minutes following tail vein injection[2]. In these experiments, hepatobiliary clearance was validated 24 hours post-tail vein injection of PEG-CPNPs, and showed the progression of signal from the liver and through the intestine as fecal matter (FIG. 6). Overall, it has been demonstrated that the transferrin receptor-targeted CPNPs were effective and selective in imaging cancerous tissues in an in vivo model of breast cancer.

Figure 7A:
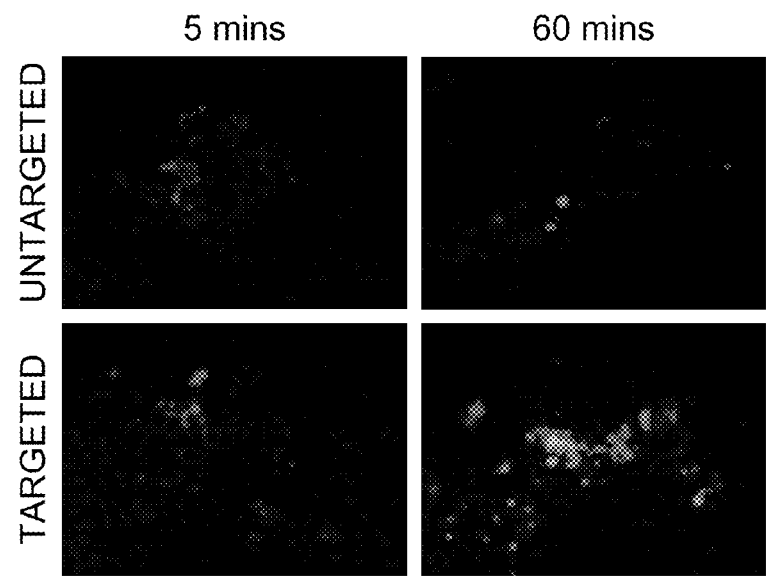
FIG. 7A-B illustrates that gastrin bioconjugated $CCK_2$-receptor-targeted CPNPs effectively targeted human BxPC-3 pancreatic cancer cells. BxPC-3 cells were exposed to flourescein-loaded untargeted PEG-CPNPs or Gastrin-10-PEG-CPNPs, for 5 min. followed by exchange to fresh media for 55 min, or exposure for 60 min. 7A: Cells were fixed and visualized by microscopy. 7B: Cells were fixed and analyzed by flow cytometry with graphs representing 10,000 collected events per sample.

Evaluation of BxPC-3 Pancreatic Cell Targeting by Gastrin-10 Conjugated $CCK_2$ Receptor-Targeted CPNPs In Vitro:

Increased surface expression of $CCK_2$ receptors on pancreatic tumors, and cell lines, was targeted by CPNPs coupled via a PEG maleimide linker to a short gastrin peptide (gastrin-10-PEG-CPNPs). (This moiety was chosen because it is shorter than the biologically active form, gastrin-17, but preserves targeting specificity) BxPC-3 human pancreatic cancer cells were treated with gastrin-10-PEG-CPNPs or untargeted PEG-CPNPs for 5 or 60 minutes, followed by a replacement of media for 55 minutes or no change, respectively. Cells were fixed and visualized using a fluorescence microscope set up to analyze a broad range of fluorescence simultaneously. Only BxPC-3 cells exposed for 60 minutes to gastrin-10-PEG-CPNPs, and no media exchange, displayed fluorescent staining (FIG. 7A). The observed fluorescence was green and blue, indicative of the pH-dependent degradation of CPNPs as they internalize in the endosomal-lysosomal pathway, and release the encapsulated dye (fluorescein). Fluorescein displays a complex pH-dependent equilibrium and emission from its two fluorescent ionic forms, the monoanion and dianion.[26, 27] In higher pH environments, such as that within the CPNPs and physiological solutions, the significant emission wavelength is from the dianion (peak excitation 495 nm, green). As pH drops below 6.5, the molecule is protonated to its monoanionic form which is excited in the blue (450 nm). Thus, emission signals from the fluorescein-encapsulating CPNPs shift from green toward blue as fluorescein molecules experience the pH drop characteristic of the endosomal-lysosomal pathway into the cells, resulting in the dissolution of the particles and release of the fluorophore into the lower pH environment of late stage endosomes.

Figure 7B:
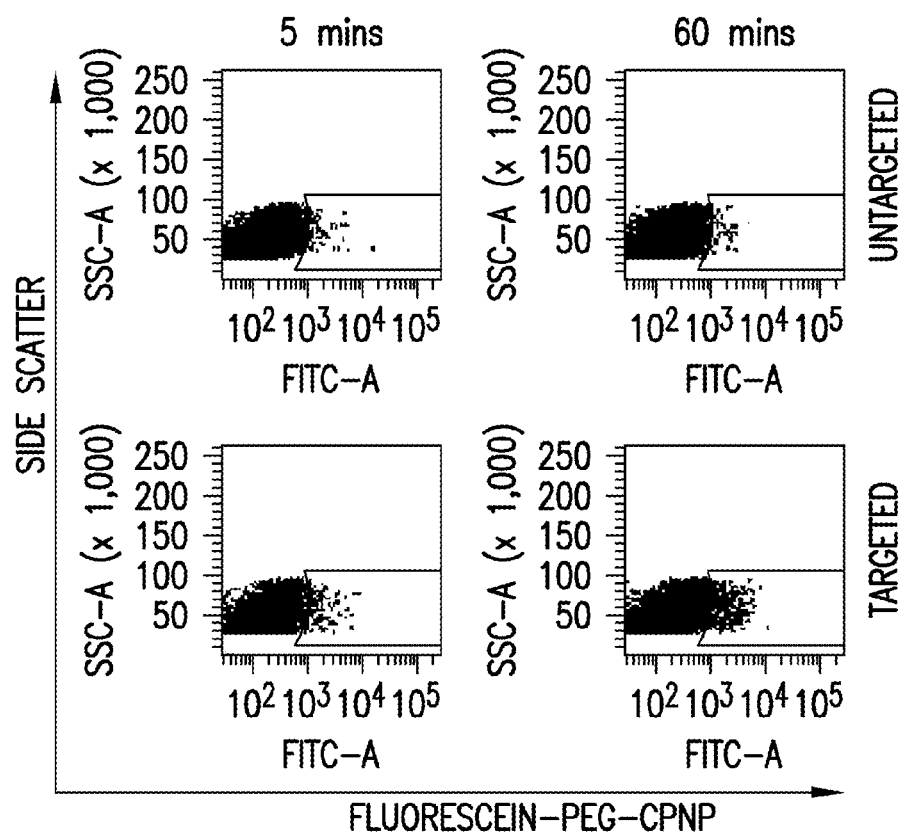

Alternatively, BxPC-3 cells were exposed, fixed, and analyzed via flow cytometry (FIG. 7B). This further showed that gastrin-10-PEG-CPNPs (60 minutes exposure) targeted BxPC-3 cells while untargeted PEG-CPNPs did not.

Figure 8A:
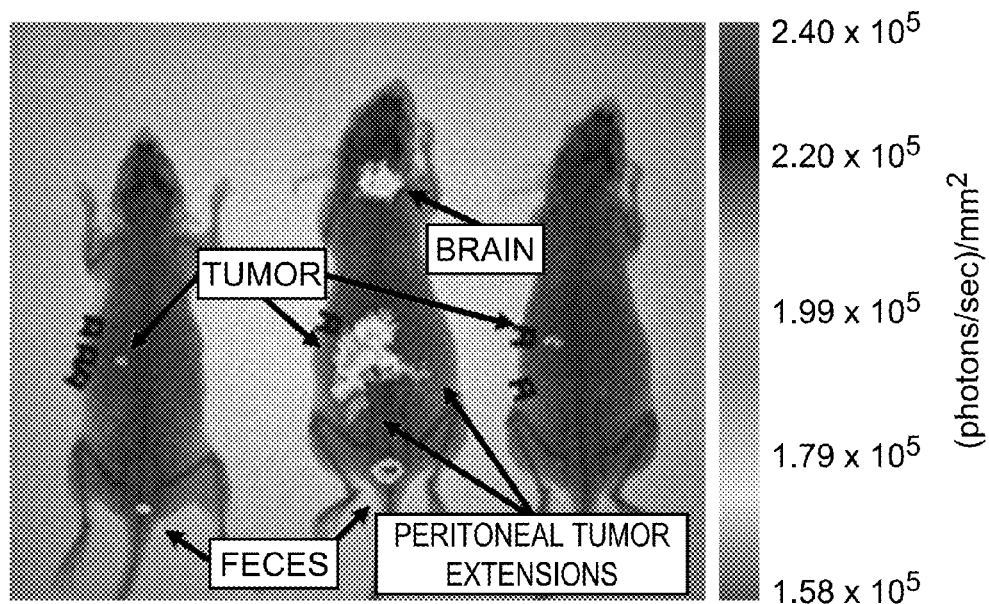
FIG. 8A-B illustrates targeting gastrin receptors in an in vivo orthotopic-tumor model of pancreatic cancer. Human BXPC-3 pancreatic cancer cells were xenografted orthotopically into athymic nude mice. 8A: One week following engraftment, ICG-loaded CPNPs were administered systemically via tail vein injection and near-infrared images were taken 96 hours post-injection. From left to right, mice receiving: (i) ICG-loaded, PEG-CPNPs, (ii) ICG-loaded, Gastrin-10-PEG-CPNPs (covalently coupled), or (iii) ICG-loaded, Pentagastrin-Avidin-CPNPs. 8B: Excised, tumor-bearing pancreas from each mouse and excised brain (mouse ii). All images are representative of at least four independent experiments.
Figure 8B:
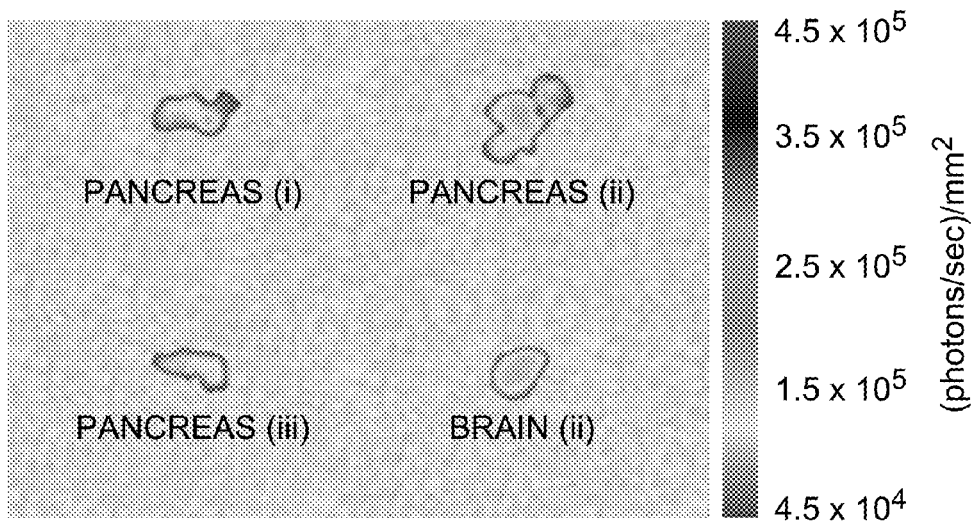

Evaluation of Pancreatic Cancer-Targeted CPNPs In Vivo:

Evaluation of pancreatic cancer-targeted CPNPs in vivo indicates that the untargeted, PEG-CPNPs effectively accumulated by EPR 24 h post-tail vein injection within small BXPC-3 tumors within the pancreas (FIG. 8A), and these whole animal images were confirmed by excision of the pancreas (FIG. 8B). Pentagastrin-Avidin-CPNPs (iii), using the avidin-biotin coupling approach, also targeted the pancreatic tumors (FIG. 8). However, the gastrin-10-PEG-CPNPs (ii) proved to be much more successful at targeting the pancreatic tumors (FIG. 8A), including peritoneal extensions of the primary tumor, as well as the brain, which is also rich in $CCK_2$ receptors[14]. Targeting of the gastrin-10-PEG-CPNPs to the brain was confirmed by excising and imaging the brain during necropsy (FIG. 8B).

An advantage of the later targeting approach is the covalent attachment of the targeting moiety (gastrin-10), eliminating the possibility of non-specific avidin interactions in vivo, as well as the PEG, which permits improved systemic retention and decreased immune-reactivity[2]. It is also possible that the presence of avidin on the CPNPs does not permit crossing of the blood-brain barrier, whereas the PEG-maleimide bioconjugation for gastrin-10 may permit penetration of the blood-brain barrier. The challenge in the prior art of delivering a blood-borne therapeutic to the brain across the blood brain barrier is well known. The present invention overcomes this problem and is one of the most important aspects of the invention. It is noteworthy that the untargeted PEG-CPNPs did not display any significant brain accumulation in this study. A recent work comparing interleukin-13-targeted nanoliposomes to untargeted nanoliposomes in a cranial model of glioblastoma showed that only targeted nanoliposomes moved significantly across the blood-brain-barrier[28]. The results presented in this patent document, although using a different target and different nanoparticles ($CCK_2$ receptor-targeted CPNPs), corroborates the findings by others that targeted nanoparticles can cross the blood-brain-barrier[25]. Importantly, the CPNPs are biocompatible, and it has been previously shown that they exhibited no specific detrimental effects toward neurons[3]. This important result was confirmed in these experiments, as no mice receiving any CPNPs showed signs of neurological deficits. Overall, the inventive bio-conjugated CPNPs and their method of use demonstrate that the CPNPs can be effectively targeted to $CCK_2$ receptors in vivo in a model of pancreatic cancer, and further demonstrate the potential for targeting across the blood-brain-barrier.

Targeting of Leukemia Stem Cell for Photodynamic Therapy:

Photodynamic therapy (PDT) has been described as an alternative to chemotherapy or radiation therapy in the treatment of malignant tumors[6]. PDT consists of three components: a photosensitizer, light, and oxygen. When exposed to light of a specific wavelength, a photosensitizer is excited, and a subsequent energy transfer to molecular oxygen produces singlet oxygen. Highly reactive singlet oxygen rapidly reacts with nearby cellular components, ultimately leading to cell death. As noted earlier, ICG may be encapsulated in CPNPs and currently is FDA approved as a contrast agent and works as a PDT agent upon illumination. CD117, a receptor tyrosine kinase, also known as c-kit, is the receptor for stem cell factor (SCF), and is normally internalized by ligand binding. CD117 internalization is dependent on tyrosine kinase activity, and this process has been shown to be important to the pro-growth signaling mechanisms elicited by SCF. ICG-loaded CPNPs were bioconjugated to anti-CD117 antibodies targeting surface features expressed on LSCs. Flow cytometry, was used to verify the ability of anti-CD117 antibody-coupled-PEG CPNPs to target cells of interest. As also noted earlier, CPNPs internalized into the endosomal-lysosomal pathway degrade and release ICG.

Figure 9:
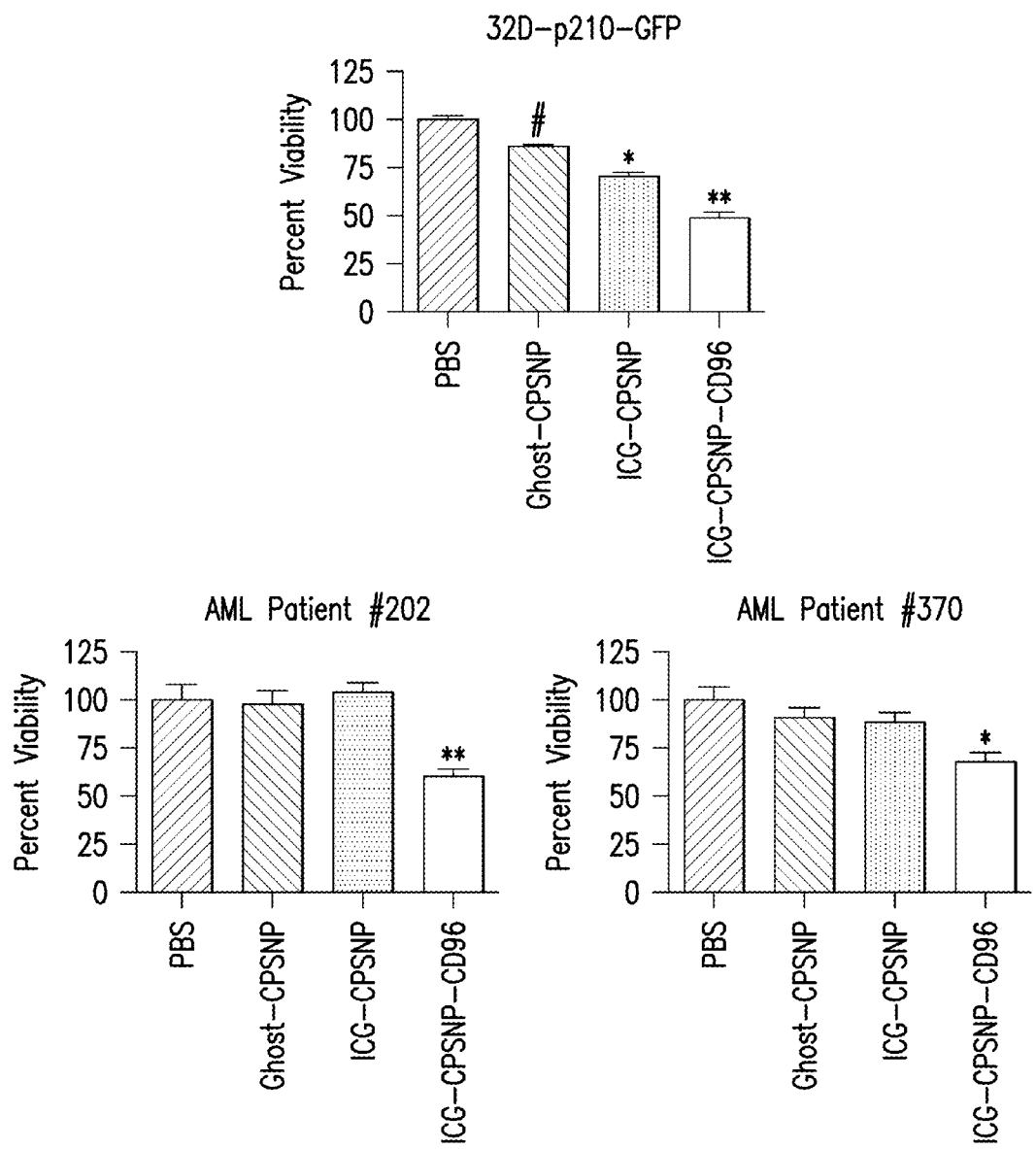
FIG. 9 illustrates the efficacy of targeted ICG-CPNP PDT in vitro. (A) 32D-p210-GFP chronic myeloid leukemia cells were treated with PBS, empty (ghost)-CPNPs, ICG-loaded CPNPs, or CD117-targeted ICG-loaded CSNPs followed by NIR-laser treatment. (B) Cells from a human acute myeloid leukemia patient (#202) were treated with PBS, empty (ghost)-CPSNPs, ICG-loaded CPSNPs, or CD96-targeted ICG-loaded CPSNPs followed by NIR-laser treatment. (C) CD96-targeted ICG CPSNP PDT was evaluated in a similar manner with cells from another human acute myeloid leukemia patient (#370).
Figure 9A:
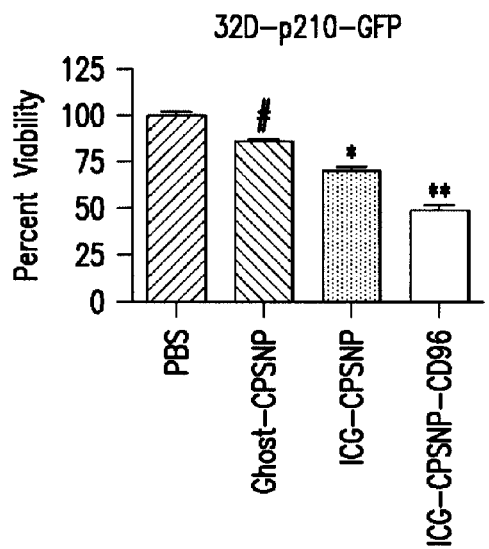
Figure 9B:
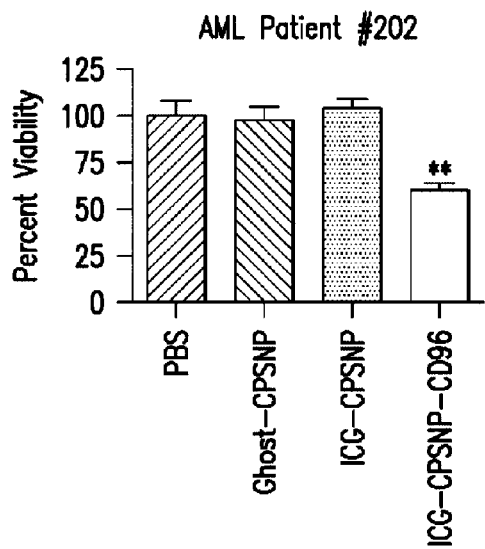
Figure 9C:
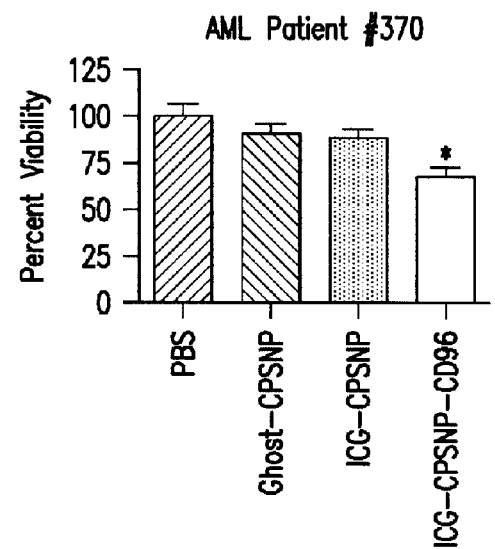

Targeting In Vitro:

In an in vitro model, 32D-p210-GFP murine CML cells, and human AML patient cells, were evaluated for sensitivity to PDT utilizing ICG-loaded CPNPs. (FIG. 9) Not surprisingly, PDT using non-targeted CPNPs loaded with ICG had only minimal, yet significant, efficacy in 32D-p210-GFP cells (30% reduction in viability), and absolutely no efficacy in both AML patient samples evaluated. In contrast, PDT utilizing anti-CD117-targeted CPNPs loaded with ICG exerted a profound and significant anti-leukemic effect on 32D-p210-GFP cells (51% reduction in viability), an effect that was also significantly different from that observed with untargeted CPNPs loaded with ICG. A robust and significant anti-leukemic effect was observed with PDT of two AML patient samples utilizing CD96-targeted CPSNPs loaded with ICG (40% and 33% reductions in viability of samples). Altogether, these results show that targeted therapy, and in particular LSC-targeted therapy utilizing bio-conjugated ICG-loaded CPNPs can improve the efficacy of PDT.

Figure 10:
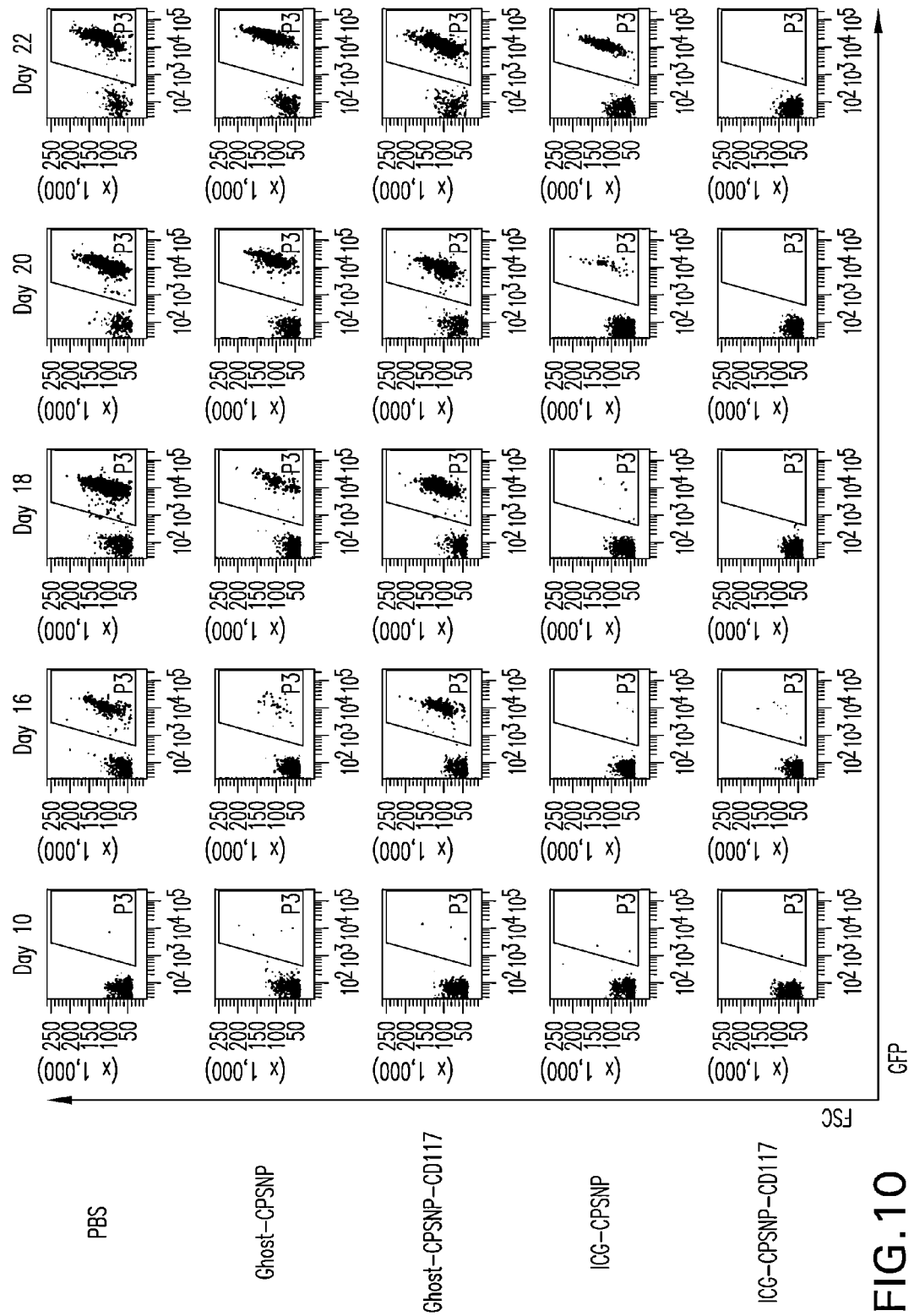
FIG. 10 illustrates that the leukemia burden is reduced by CD117-targeted ICG-CPNP PDT in vivo. Leukemia was established in C3H/HeJ mice with 32D-p210-GFP cells, and mice were treated with PBS, empty (ghost)-CPNPs, ICG-loaded CPNPs, or CD117-targeted ICG-loaded CPNPs followed by NIR-laser treatment. The leukemia burden was followed by routine flow cytometry analysis of GFP+ leukemic cells in the blood. Representative flow cytometry dot plots are shown.
Figure 11:
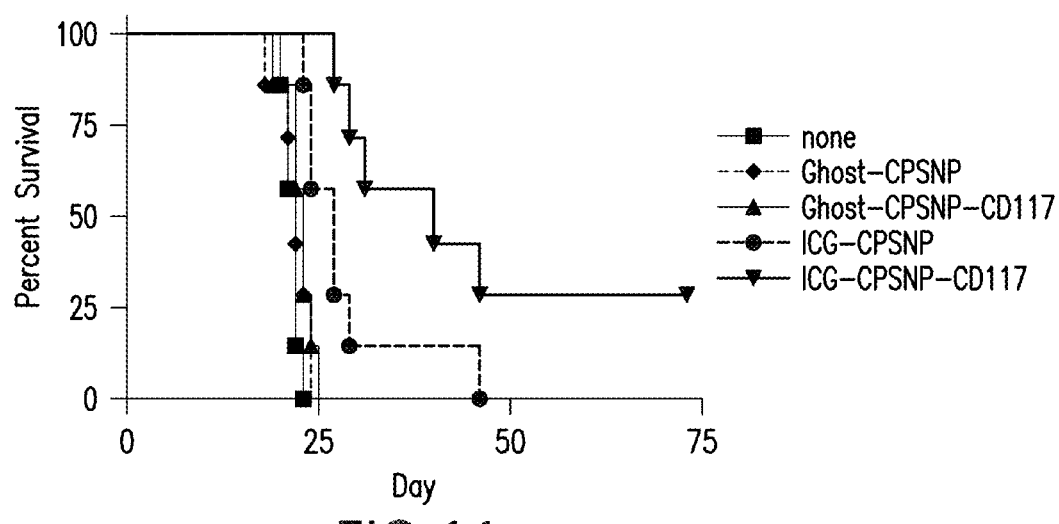
FIG. 11 illustrates that survival is extended by CD117-targeted ICG-CPNP PDT in vivo. Leukemia was established in C3H/HeJ mice with 32D-p210-GFP cells, and mice were treated with PBS, empty (ghost)-CPNPs, ICG-loaded CPNPs, or CD117-targeted ICG-loaded CPNPs followed by NIR-laser treatment and survival was monitored.

Targeting In Vivo:

Anti-CD117-PEG-ICG-CPNPs were employed in an in vivo murine model of CML. CPSNPs were diluted approximately 1:10 into PBS (200 nM pre-injection concentration of ICG), or controls, injected systemically into the lateral tail vein, and were followed immediately by 12.5 J/cm$^2$ laser NIR irradiation of the spleen. PDT utilizing non-targeted CPNPs loaded with ICG effectively slowed leukemia progression in vivo as evidenced by a significantly slower growth of 32D-p210-GFP cells in the murine model of CML (FIG. 10). This translated to a significant increase in the lifespan of these animals (FIG. 11). These results demonstrated that PDT using ICG-loaded CPNPs was efficacious in an in vivo model of CML, despite an inability of the untargeted CPNPs to accumulate via enhanced permeability and retention. Most importantly, PDT utilizing LSC-targeted CPSNPs loaded with ICG evoked a robust anti-leukemic effect. In particular, anti-CD117-targeted CPNPs loaded with ICG after PDT illumination effectively blocked an increase in leukemic cells in the blood (FIG. 10). This blockade of leukemic cell proliferation in vivo correlated with a profound and dramatic extension in survival (FIG. 11) including leukemia-free survival.

Bioconjugation of Systemically Targeted CPNPs:

The ability to target nanodelivery systems to specific tissues is important in the development of improved therapeutics for diseases such as cancer. In many studies and clinical circumstances, the efficacies of treatment are limited or the off-target effects are dramatic. Nanoscale therapeutics help to minimize these problems by concentrating higher doses of therapeutic agents in the target tissues while reducing the concentration of therapeutic agents systemically.

In the prior art it has been shown that molecular-specific therapeutics, or targeted therapeutic delivery systems are highly efficacious and may even help to overcome complicating circumstances such as multidrug resistance[11]. Often, prior art studies were restricted to in vitro models. However, the true test for active targeting requires in vivo models, in which the delivery modality is administered systemically, with the nanodelivery system allowed to freely circulate to localize in the desired tissue to establish efficacy of the targeting strategy and delivery system. This inventions described in this patent document demonstrate for the first time the bioconjugation of targeting moieties to CPNPs to effect systemic targeting in a subcutaneous, an orthotopic, and haemopoetic in vivo model using the CPNP nanodelivery system.

The CPNPs utilized for bioconjugation were engineered specifically as non-toxic, resorbable, biocompatible nanoscale delivery vehicles. It has been previously shown that a variety of molecules, including dyes that could be used in tumor detection and photodynamic therapy, or hydrophobic antineoplastic agents such as ceramide could be encapsulated[1-3] in the CPNPs. Until now in the prior art, CPNPs have relied on passive accumulation via enhanced permeation retention effect, to 'target' solid tumors and had not been employed against non-solid tumors. For the first time, the disclosures in this patent document demonstrate that surface targeting molecular moieties can be successfully bioconjugated to the CPNPs, via synthetically appropriate and distinct coupling methods, and that these bioconjugated CPNPs can effectively target select tissues and stem cells via surface feature targeting/recognition. Specifically, breast cancer tumors were targeted in vivo by targeting transferrin receptors, orthotopic pancreatic cancer tumors were targeted in vivo by targeting gastrin receptors, and leukemic stem cells were targeted in vivo by CPNPs bearing an anti-CD117 antibody (an anti-CD96 antibody in the case of human patient samples in vitro).

The observation in the prior art was also confirmed that the untargeted, PEG-CPNPs could accumulate moderately yet could be effectively imaged within small orthotopic pancreatic tumors, extending the diagnostic imaging capability and therapeutic delivery capabilities to one of the more evasive cancers. In addition, it is demonstrated that gastrin-receptor targeted CPNPs could cross the blood-brain barrier, which may expand the utility of the CPNPs to therapeutics targeted to glioblastoma or even to neurodegenerative or psychiatric disorders.

Even though systemically targeted bioconjugated CPNPs can be used to target-specific receptors or ligands on cancer cells, there may still be obstacles, as these receptors may still be expressed on other tissues. As a case in point to alleviate this short-coming, CPNPs can potentially be 'loaded' with selective gene therapies or agents to become cancer-specific. For example, although $CCK_2$ receptors are present in both malignant and some normal tissues, only the pancreatic cancer cells produce endogenous gastrin[29]. The acid secreting parietal cells of the stomach, imaged as described in this patent document with ICG-loaded, gastrin-10-PEG-CPNPs (covalently coupled), or ICG-loaded, Pentagastrin-Avidin-CPNPs (non-covalently coupled), do not produce endogenous gastrin. The only nonmalignant cells that produce gastrin in adults are the G-cells of the stomach antrum; and, the G-cells do not possess $CCK_2$ receptors[30,31]. Therefore, loading the CPNPs with a gene therapy agent (i.e., siRNA) or a gastrin antagonist will be effective in treating cancer cells without harming noncancerous cells.

It been shown in the prior art that down regulation of endogenous gastrin expression using RNA interference techniques significantly inhibits growth of pancreatic cancer tumors and metastases[32, 33]. One problem with using gene therapy in animals and in humans has been in finding delivery systems that would protect the siRNA from degradation in the peripheral circulation. Since siRNAs are readily degraded by nucleases in the peripheral blood and tissues, mechanisms for delivery have been an active area of recent investigation. Viral vectors, especially the adeno-associated viruses (AAVs) and the adenoviruses have been under investigation; however, hepatotoxicity and immunogenicity have been reported[34]. Based on the teachings in this patent document, a tissue-specific and cancer-selective vehicle such as siRNA-loaded CPNPs coupled for receptor targeting can be created and would be ideal as cancer therapeutics. It should be noted that virtually any antibody is suitable for use as a targeting moiety. Similarly, a wide range of peptides are suitable for use in the present invention.

Altogether, the successful bioconjugation of selective surface targeting moieties to CPNPs using a variety of coupling approaches has been disclosed demonstrating the effectiveness, selectivity, and utility in three separate in vivo models. The techniques disclosed will allow the further development of the CPNPs to target a diversity of disorders, including several poor prognosis cancers.

EXPERIMENTAL PROCEDURES

Preparation of Nanoparticles

CPNPs were prepared by the microemulsion technique and van der Waals-HPLC that have been previously described[1-4]. Cyclohexane ($C_6H_{12}$, 99%, BHD Chemical Co.), Igepal CO-520 ($C_{13}H_{20}O(C_2H_4O)_{n=5}$, Rhodia Chemical Co.), and deionized $H_2O$ were used to prepare the microemulsions. Calcium chloride ($CaCl_2.2H_2O$, Sigma-Aldrich Co.), disodium hydrogen phosphate ($Na_2HPO_4$, Sigma Aldrich Co.), and sodium metasilicate ($Na_2SiO_3$, Sigma-Aldrich Co.) were used as particle precursors. Disodium hydrogen citrate dihydrate ($HOC(COOH)(CH_2COONa)_2.2H_2O$, Sigma-Aldrich Co.) was used as the dispersant. Indocyanine green (ICG) (TCI America Co.) was used as the near infrared fluorophore in the CPNPs for the animal trials, while fluorescein sodium salt (Sigma-Aldrich Co.) was the visible fluorophore encapsulated for flow cell and in vitro experiments. Neat ethanol was purchased from VWR International. All other chemicals were obtained from Sigma-Aldrich Co., unless otherwise noted.

Two separate Microemulsions (1 and 2) were formed with a cyclohexane/Igepal CO-520/water system. The molar ratio of water to surfactant was 4. A 650 µl of $1\times10^{-2}$ M $CaCl_2$ in $CO_2$-free deionized $H_2O$ was added to 14 ml of a 29 volume percent solution of Igepal CO-520 in cyclohexane to form Microemulsion 1. Similarly, 65 µl of $6\times10^{-2}$M disodium hydrogen phosphate ($Na_2HPO_4$) with 65 µl of $8.2\times10^{-3}$ M sodium metasilicate ($Na_2SiO_3$) in $CO_2$-free deionized $H_2O$ (pH 7.4) was added to 14 ml of a 29 volume percent solution of Igepal CO-520 in cyclohexane to form Microemulsion 2. A 520 µl aliquot of 0.01 M ICG in $CO_2$-free deionized $H_2O$ was added into Microemulsion 2 so that the final $H_2O$ volume matched that in Microemulsion 1 (650 µL), hence retaining the water to surfactant ratio in each. The individual microemulsions were allowed to equilibrate for 1 hour before 1 and 2 were mixed to form Microemulsion 3. Microemulsion 3 was allowed to undergo micellar exchange for 2 minutes, during which time doped CPNPs precipitated in the micelles. A 225 µl aliquot of $1\times10^{-2}$ M sodium citrate was added to Microemulsion 3 and allowed to react for 15 minutes. After adding the dispersant, the reverse micelles were dissolved with 50 ml of ethanol adjusted with 1 M KOH before laundering via the van der Waals-HPLC[1-4].

The unwashed CPNP suspension was loaded onto a silica HPLC (high performance liquid chromatography) column after the micelles had been dissolved with ethanol; the free organic was laundered with ethanol adjusted with 1 M KOH as the eluent; finally, the particles were eluted using 70:30 ethanol:water by volume. During the washing step, the dye content was monitored at an absorption of 785 nm or 495 nm for ICG or fluorescein respectively. The ethanol washing was continued until the detector reached baseline indicating removal of the excess dye. The first major peak was collected. The precursor and HPLC solutions were prepared with $CO_2$-free deionized $H_2O$ to avoid carbonate contamination in the CPNPs. All solution pH measurements were performed using a Sentron ISFET pH probe calibrated against aqueous standards.

Bioconjugation of CPNPs:

Avidin Coupling:

To bioconjugate the CPNPs with avidin, a 1 ml aliquot of CPNPs in their 70% ethanol solution was first dried under argon and covered from light until all of the solvent evaporated and only the CPNPs remained. This dried sample was then reconstituted back to 1 ml with the addition of 1 ml PBS (0.01 M phosphate buffer, 0.14 M NaCl, 0.01 M KCl at pH 7.4). This was then followed by the addition of 1 ml of 20 mg/ml 1-ethyl-3-[3-dimethylaminopropyl]-carbodiimide hydrochloride (EDCI) (Sigma-Aldrich Co.) and 1 ml of 6 mg/ml avidin (Rockland Immunochemicals Inc.). Excess avidin was added in order to ensure the surface saturation of CPNPs. This reaction mixture was finally incubated at 35° C. for 24 hours in the dark with continuous stirring at 600 rpm.

After 24 hours, the reaction mixture was centrifuged (Marathon 22K Centrifuge; Fisher Scientific Co.), filtered with a 100 kDa centrifuge filter device (Amicon Ultra-4, PLHK Ultracel-PL Membrane; Millipore Co.) to remove excess unconjugated avidin. Prior to use, the filtration membrane of the centrifuge filter device was washed with deionized $H_2O$ in order to minimize non-specific binding. A total of three centrifuge filtrations, each at 1000×g for 30 minutes, were performed in order to maximize the removal of excess unconjugated avidin. After each centrifuge filtration step, the final volume of the retentate solution was brought back to the starting volume by the addition of PBS.

Multiple types of commercially available centrifuge filter devices, with different filtration membrane materials and chemistry, were evaluated to obtain minimal non-specific adsorption and optimal washing of the CPNPs. The Millipore Amicon centrifuge filter device with 100 kDa nominal molecular weight limit Ultracel YM-100 regenerated cellulose membrane was identified as the product of choice. Centrifuge filter devices with a polyethersulfone filtration membrane were not feasible for this investigation due to significant non-specific binding of the CPNPs to the filtration membrane.

The conjugation of biotinylated human holotransferrin or biotinylated anti-CD71 antibody to Avidin-CPNPs permits targeting of the transferrin receptor; the conjugation of biotinylated pentagastrin to Avidin-CPNPs permits targeting of the gastrin receptor (FIG. 1A). A 1 ml aliquot of 3.2 mg/ml biotin conjugated human holotransferrin (Invitrogen Co.), 0.20 ml of 1 mg/ml biotin conjugated anti-CD71 antibody (GeneTex Inc.), or 0.50 ml of 1 mg/ml biotin conjugated pentagastrin (Bachem Co.) (in 0.1 N $NH_4OH$) was added to 1 ml of Avidin-CPNP complex. This reaction mixture was stirred at 600 RPM for 60 minutes at room temperature. The resulting biomolecule-Avidin-CPNP complex was then filtered to remove excess unconjugated biomolecule (human holotransferrin, anti-CD71 antibody, or pentagastrin). Human holotransferrin-Avidin-CPNPs and anti-CD71-Avidin-CPNPs were filtered by tangential flow diafiltration using a 500 kDa molecular weight cut-off (MWCO) MicroKros hollow fiber tangential flow diafiltration device (Spectrum Laboratories Inc.). Pentagastrin-Avidin-CPNPs were centrifuge filtered with a 100 kDa centrifuge filter device (Amicon Ultra-4, PLHK Ultracel-PL Membrane; Millipore Co.). All the biomolecule-Avidin-CPNP samples were filtered three times in order to maximize the removal of excess unconjugated biomolecule. After each filtration step, the final volume of the retentate solution was brought back to the starting volume by the addition of PBS.

Maleimide Coupling:

The conjugation of gastrin-10 to CPNPs via the PEG-maleimide coupling strategy (FIG. 1B) permits targeting of the gastrin receptor. A 9 ml aliquot of citrate-CPNPs was chemically conjugated with maleimide polyethylene glycol amine (PEG maleimide; JenKem Technology Inc.), through the ethyl-N-(3-dimethylaminopropyl)-N' hydrochloride carbodiimide reaction (EDCI, Fluka BioChemika ≥99.0% (AT); Sigma-Aldrich Co.). The sample was first stirred at 550 rpm on a combined magnetic stir/hot plate set to 50° C. In a drop wise manner, 1 ml of EDCI (1 mg/ml) followed by 1 ml of PEG-maleimide (10 mg/ml), both in aqueous solutions of $CO_2$-free deionized $H_2O$ (pH 7), were added to the sample under continuous stirring, to produce a calculated 6-fold excess for monolayer surface coverage. The particles were left to react for 15 hours at 50° C. to form amide linkages between the carboxylate surfaces and the PEG-maleimide. The mixture was then centrifuge filtered through a 100 kDa filter (Amicon PLHK Ultra PL-4 Membrane; Millipore Co.) at 5000 g for 2 minutes to remove any excess EDAC and unreacted PEG-maleimide. The characterization of the resulting maleimide-PEG-CPNPs in the retentate showed that the CPNPs remained well dispersed after the centrifugation wash. The gastrin-10 peptide has a cysteine residue for covalent attachment. Thus, the gastrin-10 was added at a 5:1 molar excess to the maleimide-PEG-CPNPs. This solution was incubated overnight at 4° C., protected from light, to produce Gastrin-10-PEG-CPNPs.

Sulfo-NHS-PEG Coupling:

In brief, citrate-functionalized CPNPs were activated by 1-ethyl-3-(3-dimethylaminopropyl) carbodiimide (EDAC), and then reacted with sulfo-NHS to form a high-yield, semi-stable intermediate. Centrifugation was used to remove EDAC while PEG, with both amine and citrate functional groups, was reacted with the sulfo-NHS ester-containing CPNPs. This synthetic process was repeated with the citrate-PEG functional terminals of the PEGylated CPNPs to generate sulfo-NHS ester-containing PEGylated CPNPs, which after further centrifugation to remove EDAC, readily reacted with anti-CD117 antibodies to form specifically targeted, anti-CD117-PEG-CPNPs.

Polyethylene glycol (PEG) was conjugated to the surface of the CPNSPs using an amide linkage between the amine termination of the PEG and the carboxyl group from the citrate on the surface of the CPSNPs. The conjugation procedure was modified from Altinoglu et al 2008. The addition of the N-hydroxysulfosuccinimide (Sulfo-NHS) increased the efficiency of forming the amide bond.

250 μl of EDAC (2 mg/ml CO2 free DI water) is added to 3 ml of citrate terminated CPSNPs dispersed in 70/30 ethanol/water. After 5 minutes, 250 μl of Sulfo-NHS (15 mg/ml CO2 free DI water) is added to the solution. After another 5 minutes, a 250 μl solution of methoxy-PEG-amine (15 mg/ml) and 250 μl solution of carboxy-PEG-amine (2 mg/ml) are added simultaneously. The particles are reacted for 15 hours at 50 degrees C. while stirring.

In contrast to the PEG-maleimide bioconjugation scheme, the carboxy terminal group of the carboxy-PEG-amine was used to conjugate antibodies to the PEG surface of the CPNPs. 250 μl EDAC (1 mg/ml) is added to carboxy-PEGylated CPSNPs while stirring at room temperature (25 C). After 5 minutes, 250 μl Sulfo-NHS (1 mg/ml) is added to the solution. The antibody solutions are added after 5 more minutes. For the conjugation of anti-CD96, 25 μl of a 6.67 μM solution is diluted into 225 μl $CO^2$ free water and added into the particle solution. For the conjugation of anti-CD117, 5 μl of a 1.3 μM solution is diluted into 245 μl CO2 free water and added to the particle suspension.

Characterization of Nanoparticles:

Particle size distributions for the CPNPs were obtained through dynamic light scattering (DLS) using a Malvern Nano-S Zetasizer. Transmission electron microscopy (TEM) was performed using a JEOL JEM 1200 EXII instrument on dried nanoparticles prepared on a carbon film grid with a copper backing. To verify that avidin was grafted on the CPNPs, zeta potential distributions were obtained using a Brookhaven ZetaPALS zeta potential analyzer. To quantify and test the bioactivity of avidin grafted on CPNPs, a fluorometric assay for avidin-biotin interaction based on the displacement of the fluorescent probe 2-Anilinonaphthalene-6-sulfonic acid (2,6-ANS) was utilized (Mock et al., 1985). The reaction scheme for the 2,6-ANS assay is illustrated in FIG. 3.

A 4.85 mg/ml solution of 2,6-ANS (Molecular Probes, Invitrogen Co.) was prepared in 1 ml of deionized $H_2O$. A 24 μg/ml solution of biotin was prepared in 10 ml of deionized $H_2O$ to produce the biotin solution for the assay. The 2,6-ANS solution, followed by the biotin solution, was titrated in 0.50 μl aliquots into the avidin-CPNP solution to obtain a sufficient number of data points. The reaction mixture was stirred for one minute after the addition of each aliquot to the avidin-CPNP solution to allow enough time for a homogeneous reaction mixture and to maintain consistency with respect to reaction time throughout the experiment. The fluorescence spectra were recorded with a PTI fluorometer in which emitted radiation is collected at 90 degrees with a photomultiplier tube (PMT) detector. The sample is excited by a xenon arc lamp whose illumination passes through a 5 nm bandwidth slit and a monochrometer to select the excitation wavelength. For the emission scan, the excitation wavelength was set to 328 nm and the emission wavelength range was set to 350-625 nm.

Cell Culture:

Human MDA-MB-231 breast cancer cells were cultured in DMEM supplemented with 10% fetal bovine serum (FBS) and 1% antibiotic/antimycotic solution (Invitrogen, Carlsbad, Calif.). Human BxPC-3 pancreatic cancer cells were cultured in RPMI-1640 supplemented with 10% FBS and 1% antibiotic/antimycotic solution. All cell cultures were maintained at 37° C. and 5% $CO_2$. Cells were harvested by trypsin/EDTA detachment for subculture or tumor engraftment.

Fluorescence Microscopy:

Cells were grown on cover slips under normal media conditions, and then incubated with targeted or untargeted CPNPs followed by a media exchange. Cells were fixed in 2% (w/v) paraformaldehyde, and mounted onto glass slides. Cells were visualized using a Nikon Eclipse E400 microscope through a 40× objective using a combination Nikon DAPI/FIT-C filter cube and recorded on a Nikon Coolpix 995 digital camera.

Flow Cytometry:

Cells were detached from tissue culture-ware, surface Fc receptors blocked with appropriate IgG, incubated with specific antibodies (anti-human CD71-FITC or-PE, eBiosciences, San Diego, Calif.), and fixed in 2% (w/v) paraformaldehyde. Samples were analyzed on a BD Biosciences (San Jose, Calif.) LSR II Special Order flow cytometer in the Penn State College of Medicine Flow Cytometry Core, utilizing appropriate compensation controls. Data analysis was performed using BD Biosciences FACS Diva software.

In Vivo Tumor Xenograft Breast Cancer:

All animal procedures were approved by the Pennsylvania State University Institutional Animal Care and Use Committee. To evaluate the breast cancer-targeted CPNPs in vivo, xenografted MDA-MB-231 human breast cancer cells injected subcutaneously into athymic nude mice were used. Four to six week old female athymic nude mice were purchased from Harlan (Indianapolis, Ind.). Subcutaneous breast cancer xenografts were prepared as previously described[2]. Briefly, $10^7$ MDA-MB-231 cells, prepared in 100 μliter of growth media, were engrafted by subcutaneous injection. Once the tumors established (one week), CPNPs suspended in sterile isotonic saline were injected into the tail veins of the mice, and routine images were taken over a 96 hour period. As controls, free ICG or ICG-loaded, PEG-CPNPs (non-targeted) were alternatively injected, these were diluted to ensure that equivalent ICG concentrations (as determined by absorption spectroscopy) were administered to each mouse.

In Vivo Orthotopic Tumor Pancreatic Cancer:

To evaluate the pancreatic cancer-targeted CPNPs in vivo, an in vivo model of pancreatic cancer, BXPC-3 human pancreatic cancer cells, were orthotopically injected into the pancreas of athymic nude mice. Orthotopic pancreatic cancer tumors were prepared as previously described[30]. Briefly, mice were fully anesthetized with a mixture of ketamine-HCl (129 mg/kg) and xylazine (4 mg/kg) and injected intramuscularly. A small incision was made in the left flank, the peritoneum was dissected and the pancreas exposed. Using a 27-gauge needle, $10^6$ BxPC-3 cells, prepared in 100 μl of Hank's balanced salt solution, were injected into the pancreas. All xenografted or orthotopic tumors were allowed to establish for one week prior to experimentation.

In Vivo Imaging:

CPNPs, or controls, were diluted into sterile isotonic NaCl and 100 μliter was injected via tail vein into tumor-bearing mice. Equivalent ICG concentrations were determined prior to injection
via absorption spectroscopy ($2 \times 10^{-6}$ M prior to dilution). Whole animal imaging was performed as previously described.[2] Briefly, anesthesia was induced and maintained by inhalation of 5% IsolSol (Vedco, St. Joseph, Mo.) in 100% oxygen. Near-infrared transillumination images (755 nm excitation, 830 nm emission, 3 minute exposure) and corresponding X-ray images were obtained with an In Vivo FX whole animal imaging station (Carestrearn Health, Rochester, N.Y.). Signal distribution relative to anatomy was illustrated by merging near-infrared and X-ray images.

REFERENCES

1. Morgan, T. T.; Muddana, H. S.; Altinoğlu, E. İ.; Rouse, S. M.; Tabaković, A.; Tabouillot, T.; Russin, T. J.; Shanmugavelandy, S. S.; Butler, P. J.; Eklund, P. C., et al. Encapsulation of Organic Molecules in Calcium Phosphate Nanocomposite Particles for Intracellular Imaging and Drug Delivery. *Nano Letters* 2008, 8, (12), 4108-4115.
2. Altinoğlu, E. İ.; Russin, T. J.; Kaiser, J. M.; Barth, B. M.; Eklund, P. C.; Kester, M.; Adair, J. H. Near-Infrared Emitting Fluorophore-Doped Calcium Phosphate Nanoparticles for in Vivo Imaging of Human Breast Cancer. *ACS Nano* 2008, 2, (10), 2075-2084.
3. Kester, M.; Heakal, Y.; Fox, T.; Sharma, A.; Robertson, G. P.; Morgan, T. T.; Altinoğlu, E. İ.; Tabaković, A.; Parette, M. R.; Rouse, S. M., et al. Calcium Phosphate Nanocomposite Particles for in Vitro Imaging and Encapsulated Chemotherapeutic Drug Delivery to Cancer Cells. *Nano Letters* 2008, 12, 4116-4121.
4. Muddana, H. S.; Morgan, T. T.; Adair, J. H.; Butler, P. J. Photophysics of Cy3-Encapsulated Calcium Phosphate Nanoparticles. *Nano Letters* 2009, 4, 1559-1566.
5. Daniels, T. R.; Delgado, T.; Helguera, G.; Penichet, M. L. The Transferrin Receptor Part Ii: Targeted Delivery of Therapeutic Agents into Cancer Cells. *Clin Immunol* 2006, 121, (2), 159-176.
6. Daniels, T. R.; Delgado, T.; Rodriguez, J. A.; Helguera, G.; Penichet, M. L. The Transferrin Receptor Part I: Biology and Targeting with Cytotoxic Antibodies for the Treatment of Cancer. *Clin Immunol* 2006, 121, (2), 144-158.
7. Omary, M. B.; Trowbridge, I. S.; Minowada, J. Human Cell-Surface Glycoprotein with Unusual Properties. *Nature* 1980, 286, 888-891.
8. Shindelman, J. E.; Ortmeyer, A. E.; Sussman, H. H. Demonstration of the Transferrin Receptor in Human Breast Cancer Tissue. Potential Marker for Identifying Dividing Cells. *Int. J. Cancer* 1981, 27, 329-334.
9. Sutherland, R.; Delia, D.; Schneider, C.; Newman, R.; Kemshead, J.; Greaves, M. Ubiquitous Cell-Surface Glycoprotein on Tumor Cells Is Proliferation-Associated Receptor for Transferrin. *Proc. Natl. Acad. Sci. U.S.A.* 1981, 78, 4515-4519.
10. Gosk, S.; Vermehren, C.; Storm, G.; Moos, T. Targeting Anti-Transferrin Receptor Antibody (Ox26) and Ox26-Conjugated Liposomes to Brain Capillary Endothelial Cells Using in Situ Perfusion. *J. Cereb. Blood Flow Metab.* 2004, 11, 1193-1204.
11. Huwyler, J.; Drewe, J.; Krähenbuhl, S. Tumor Targeting Using Liposomal Antineoplastic Drugs. *Int. J. Nanomedicine* 2008, 3, (1), 21-29.
12. Smith, J. P.; Fantaskey, A.; Liu, G.; Zagon, I. S. Identification of Gastrin as a Growth Peptide in Human Pancreatic Cancer. *Am J Physiol* 1995, 268, R135-R141.
13. Smith, J. P.; Stock, E. A.; Wotring, M. G.; McLaughlin, P. J.; Zagon, I. S. Characterization of the CCK-B/Gastrin-Like Receptor in Human Colon Cancer. *Am J Physiol.* 1996, 271, R796-R805.
14. Wank, S. A.; Pisegna, J. R.; de Weerth, A. Brain and Gastrointestinal Cholecystokinin Receptor Family: Structure and Functional Expression. *Proc. Natl. Acad. Sci. U.S.A.* 1992, 89, (18), 8691-5.
15. Kopin, A. S.; Lee, Y. M.; McBride, E. W.; Miller, L. J.; Lu, M.; Lin, H. Y.; Kolakowski, L. F., Jr.; Beinborn, M. Expression Cloning and Characterization of the Canine Parietal Cell Gastrin Receptor. *Proc. Natl. Acad. Sci. U.S.A.* 1992, 89, 3605-3609.
16. Soll, A. H.; T., B., *Receptors That Regulate Gastric Acid-Secretory Function.* 3 ed.; Raven Press: New York, 1994; Vol. 1, p 1139-1170.
17. Johnson, L. R.; McCormack, S. A., *Regulation of Gastrointestinal Mucosal Growth.* 3 ed.; Raven Press: New York, 1994; Vol. 1, p 611-642.
18. Smith, J. P.; Shih, A. H.; Wotring, M. G.; McLaughlin, P. J.; Zagon, I. S. Characterization of CCK-B/Gastrin-Like Receptors in Human Gastric Carcinoma. *Int. J. Oncol.* 1998, 12, 411-419.
19. Smith, J. P.; Liu, G.; Soundararajan, V.; McLaughlin, P. J.; Zagon, I. S. Identification and Characterization of CCK-B/Gastrin Receptors in Human Pancreatic Cancer Cell Lines. *Am. J. Physiol.* 1994, 266, R277-R283.
20. Smith, J. P.; Verderame, M. F.; McLaughlin, P.; Martenis, M.; Ballard, E.; Zagon, I. S. Characterization of the CCK-C (Cancer) Receptor in Human Pancreatic Cancer. *Int. J. Mol. Med.* 2002, 10, 689-694.
21. Jemal, A.; Siegel, R.; Ward, E.; Hao, Y.; Xu, J.; Murray, T.; Thun, M. J. Cancer Statistics. *CA Cancer J. Clin.* 2008, 58, 71-96.
22. Mock, D. M.; Langford, G.; Dubois, D.; Criscimagna, N.; Horowitz, P. A Fluorometric Assay for the Biotin-Avidin Interaction Based on Displacement of the Fluorescent Probe 2-Anilinonaphthalene-6-Sulfonic Acid. *Anal Biochem* 1985, 151, (1), 178-81.
23. Livnah, O.; Bayer, E. A.; Wilchek, M.; Sussman, J. L. Three-Dimensional Structures of Avidin and the Avidin-Biotin Complex. *Proc. Natl. Acad. Sci. U.S.A.* 1993, 90, (11), 5076-5080.
24. Morag, E.; Bayer, E. A.; Wilchek, M. Reversibility of Biotin-Binding by Selective Modification of Tyrosine in Avidin. *Biochem. J.* 1996, 316 (Pt 1), 193-199.
25. Pardridge, W. M. Brain Drug Delivery and Blood-Brain Barrier Transport. *Drug Delivery* 1993, 1, 83-101.
26. Sjoback, R.; Nygren, J.; Kubista, M. Absorption and Fluorescence Properties of Fluorescein. *Spectrochim Acta A* 1995, 6, (51), L7-L21.
27. Lakowicz, J. R., *Principles of Fluorescence Spectroscopy.* 3rd ed.; Springer: Baltimore, Md., 2006.
28. Madhankumar, A. B.; Slagle-Webb, B.; Wang, X.; Yang, Q. X.; Antonetti, D. A.; Miller, P. A.; Sheehan, J. M.; Connor, J. R. Efficacy of Interleukin-13 Receptor-Targeted Liposomal Doxorubicin in the Intracranial Brain Tumor Model. *Mol Cancer Ther.* 2009, 8, (3), 648-54.
29. Smith, J. P.; Shih, A.; Wu, Y.; McLaughlin, P. J.; Zagon, I. S. Gastrin Regulates Growth of Human Pancreatic Cancer in a Tonic and Autocrine Fashion. *Am. J. Physiol.* 1996, 270, R1078-R1084.
30. Brand, S. J.; Fuller, P. J. Differential Gastrin Gene Expression in Rat Gastrointestinal Tract and Pancreas During Neonatal Development. *J. Biol. Chem.* 1988, 263, 5341-5347.
31. Rozengurt, E.; Walsh, J. H. Gastrin, Cck, Signaling, and Cancer. *Annu. Rev. Physiol.* 2001, 63, 49-76.
32. Matters, G. L.; Harms, J. F.; McGovern, C. O.; Jayakumar, C.; Crepin, K.; Smith, Z. P.; Nelson, M. C.; Stock, H.; Fenn, C. W.; Kaiser, J., et al. Growth of Human Pancreatic Cancer Is Inhibited by Down-Regulation of Gastrin Gene Expression. *Pancreas* 2009, 38, e151-e161.
33. Smith, J. P.; Verderame, M. F.; Ballard, E. N.; Zagon, I. S. Functional Significance of Gastrin Gene Expression in Human Cancer Cells. *Regul. Pept.* 2004, 117, 167-173.
34. Grimm, D.; Streetz, K. L.; Jopling, C. L.; Storm, T. A.; Pandey, K.; Davis, C. R.; Marion, P.; Salazar, F.; Kay, M. A. Fatality in Mice Due to Oversaturation of Cellular MicroRNA/Short Hairpin RNA Pathways. *Nature* 2006, 441, 537-541.
35. Sosabowski, J.; Lee, M.; Dekker, B.; Simmons, B.; Singh, S.; Bereford, H.; Hagan, S.; McKenzie, A.; Mather, S.; Watson, S. Formulation Development and Manufacturing of a Gastrin/CCK-2 Targeting Peptide as an Intermediate Drug Product for Clinical Imaging Study. *Eur J Pharm Sci.* 2007, 31, 102-111.

We claim:
1. A process for the production of nontoxic, colloidally stable, resorbable, non-aggregating, PEG-conjugated calcium phosphosilicate nanocomposite particles having surface targeting molecular moieties conjugated to the PEG on the surface of the particles and having chemotherapeutics, gene therapy, and/or imaging agents incorporated within the particles, the process comprising the following steps:

A) forming calcium phosphosilicate nanocomposite particles doped with chemotherapeutics, gene therapy, and/or imaging agents by:
 1) preparing a first microemulsion by adding $CaCl_2$ in $CO_2$-free deionized $H_2O$ to IGEPAL CO-520 in cyclohexane;
 2) preparing a second microemulsion by adding $Na_2HPO_4$ and $Na_2SiO_3$ in $CO_2$-free deionized $H_2O$ to IGEPAL CO-520 in cyclohexane;
 3) adding chemotherapeutics, gene therapy, and/or imaging agents in $CO_2$-free deionized $H_2O$ to the first or second microemulsion;
 4) equilibrating the first and second microemulsions;
 5) mixing the first and second microemulsions to form a third microemulsion in which calcium phosphosilicate nanocomposite particles doped with the chemotherapeutics, gene therapy, and/or imaging agents precipitate;
 6) adding sodium citrate to the third microemulsion to functionalize the particles with citrate;
 7) adding ethanol to the third microemulsion to dissolve the reverse micelles;
 8) loading the third microemulsion containing the particles on a silica HPLC column;
 9) washing the particles with ethanol; and
 10) eluting the particles with 70:30 ethanol:water; and
B) conjugating the surface targeting molecular moieties to the particles by:
 1) adding EDAC to the particles dispersed in 70:30 ethanol:water to activate the particles;
 2) adding Sulfo-NHS to the particle dispersion to form a high-yield, semi-stable intermediate;
 3) removing residual EDAC by washing and filter centrifugation of the particle dispersion using 100 kDa ULTRACEL YM-100 regenerated cellulose filters;
 4) adding PEG with both carboxy and amine functional groups, both methoxy and amine functional groups, or both citrate and amine functional groups to the Sulfo-NHS ester-containing washed particles to form PEG-conjugated particles having carboxy-PEG functional terminals, methoxy-PEG functional terminals, or citrate-PEG functional terminals;
 5) adding EDAC to the PEG-conjugated particles to activate the PEG-conjugated particles;
 6) adding Sulfo-NHS to the PEG-conjugated particles to form a second high-yield, semi-stable intermediate;
 7) removing residual EDAC by washing and filter centrifugation of the PEG-conjugated particles using 100 kDa ULTRACEL YM-100 regenerated cellulose filters; and
 8) reacting the surface targeting molecular moieties with the Sulfo-NHS ester-containing PEG-conjugated particles.

2. A nontoxic, colloidally stable, resorbable, non-aggregating, PEG-conjugated calcium phosphosilicate nanocomposite particle having surface targeting molecular moieties conjugated to the PEG on the surface of the particle and having chemotherapeutics, gene therapy, and/or imaging agents incorporated within the particle made by the process of claim 1.

* * * * *